United States Patent [19]

Zimmerle

[11] Patent Number: 5,403,744
[45] Date of Patent: Apr. 4, 1995

[54] METHOD, COMPOSITION AND DEVICE FOR MEASURING THE IONIC STRENGTH OR SPECIFIC GRAVITY OF A TEST SAMPLE

[75] Inventor: Chris T. Zimmerle, Elkhart, Ind.

[73] Assignee: Miles Inc., Elkhart, Ind.

[21] Appl. No.: 217,555

[22] Filed: Mar. 25, 1994

Related U.S. Application Data

[63] Continuation-in-part of Ser. No. 19,915, Feb. 19, 1993, abandoned.

[51] Int. Cl.$^6$ ............................................. G01N 9/36
[52] U.S. Cl. ........................................ 436/2; 436/74; 436/169; 422/56
[58] Field of Search .................... 422/56–58; 436/2, 163, 164, 169, 74; 73/32 R; 427/2

[56] References Cited

U.S. PATENT DOCUMENTS 4,318,709  3/1982  Falb et al. .......................... 436/163
4,376,827  3/1983  Stiso et al. ............................ 436/2

OTHER PUBLICATIONS

Vitagliano, V., "Interaction Between Cationic Dyes and Polyelectrolytes." *Chemical and Biological Applications of Relaxation Spectrometry*, pp. 437–466 (1975), E. Wyn-Jones, Ed.

Primary Examiner—James C. Housel
Assistant Examiner—Rachel Freed
Attorney, Agent, or Firm—Roger N. Coe

[57] ABSTRACT

A method, composition and test device for determining the ionic strength or specific gravity of a test sample are disclosed. The method utilizes a test device comprising a test pad, wherein the test pad includes a carrier matrix incorporating a reagent composition capable of producing a detectable and measurable response that correlates to the ionic strength and the buffer capacity, and therefore the specific gravity, of the test sample. The reagent composition, comprising a strong polyelectrolyte, an indicator comprising: (i) a dye that is metachromatic and sensitive to pH changes, or (ii) or a combination of metachromatic dye and a pH indicator dye, in a suitable carrier, and buffered at a pH of 3 or less, is incorporated into a carrier matrix to provide a test pad of a device useful in an ionic strength or specific gravity assay of a test sample.

30 Claims, 2 Drawing Sheets

METHOD, COMPOSITION AND DEVICE FOR MEASURING THE IONIC STRENGTH OR SPECIFIC GRAVITY OF A TEST SAMPLE

CROSS-REFERENCE TO RELATED APPLICATION

This is a continuation-in-part application of U.S. Ser. No. 08/019,915, filed Feb. 19, 1993, now abandoned.

FIELD OF THE INVENTION

The present invention relates to a method, composition and test device for determining the ionic strength or specific gravity of a test sample. More particularly, the present invention relates to a method of assaying an aqueous test sample, such as urine, for ionic strength or specific gravity that: a) utilizes a reagent composition that undergoes a detectable or measurable response upon contact of the test sample with the reagent composition, and b) is essentially independent of test sample pH. The detectable response is proportional to the ionic strength and the buffer capacity of the test sample, and can be correlated quantitatively to the ionic strength and the specific gravity of the test sample. The reagent composition provides sufficient color differentiation between test samples to provide an assay for the ionic strength or specific gravity of the test sample.

BACKGROUND OF THE INVENTION AND PRIOR ART

The specific gravity of a test sample, such as urine or serum, is a measure of the relative proportions of solid material dissolved in the test sample to the total volume of the test sample. In general, the specific gravity of a test sample is a measure of the relative degree of concentration or the relative degree of dilution of the test sample. The specific gravity of many urine samples can be accurately correlated to the ionic strength, or ion concentration, of the test sample. Typically, as the number of urine components that are measured increases, the correlation of ionic strength to urine specific gravity also increases. With regard to urine samples, the assay for specific gravity helps interpret the results of the other assays performed in a routine urinalysis.

Clinically, under appropriate and standardized conditions of fluid restriction or increased fluid intake, the specific gravity of a urine sample measures the concentrating and diluting abilities of the kidneys of an individual. The specific gravity of urine ranges from about 1.005 to about 1.030, and usually is in the range from about 1.010 to about 1.025. A specific gravity of about 1.025 or above in a random first morning urine specimen indicates a normal concentrating ability of the kidneys.

Either an abnormally low or an abnormally high urine specific gravity is clinically significant. Therefore, accurate and reliable specific gravity assays of urine and other aqueous test samples must be available for both laboratory and home use. The assays must provide an accurate measurement of abnormally low and abnormally high specific gravities, such that a correct diagnosis can be made and correct medical treatment implemented, monitored and maintained.

For example, diabetes insipidus is characterized by excreting large urine volumes of low specific gravity, and is a severe example of impaired kidney concentrating ability. The urine specific gravity of individuals suffering from diabetes insipidus usually ranges between 1.001 and 1.003. Low urine specific gravity also occurs in persons suffering from glomerulonephritis, pyelonephritis, and various other renal anomalies. In these cases, the kidney has lost its ability to concentrate the urine because of tubular damage.

An abnormally high urine specific gravity also is indicative of a diseased state. For example, the urine specific gravity is abnormally high in an individual suffering from diabetes mellitus, adrenal insufficiency, hepatic disease or congestive cardiac failure. Urine specific gravity likewise is elevated when an individual has lost an excessive amount of water, such as with sweating, fever, vomiting and diarrhea. In addition, abnormally high amounts of nonionic urinary constituents, like glucose and protein, increase the urine specific gravity to 1.050 or greater in some individuals suffering from diabetes mellitus or nephrosis. Urine with a fixed low specific gravity of approximately 1.010 that varies little from specimen to specimen is known as isothenuric. This condition is indicative of severe renal damage with disturbance of both the concentrating and diluting abilities of the kidney.

In order to determine if an individual has either an abnormally high or an abnormally low urine specific gravity, and in order to help monitor the course of a medical treatment to determine its effectiveness, simple, accurate and inexpensive specific gravity assays have been developed. In general, the specific gravity of a test sample is a measurement that relates to the density of the test sample. The specific gravity is a value derived from the ratio of the weight of a given volume of a test sample, such as urine, to the weight of the same volume of water under standardized conditions (Eq. 1).

$$\text{Sp. Gr.} = \frac{\text{weight of urine}}{\text{weight of water}} \qquad \text{Eq. 1}$$

Water has a specific gravity of 1.000. Since urine is a solution of minerals, salts, and organic compounds in water, the specific gravity of urine is greater than 1.000. The relative difference reflects the degree of concentration of the urine specimen and is a measure of the total solids in urine.

Several methods are available to determine the specific gravity of urine. The most widely used method, and possibly the lease accurate, employs a urinometer. The urinometer is a weighted, bulb-shaped instrument having a cylindrical stem containing a scale calibrated in specific gravity readings. The urinometer is floated in a cylinder containing the urine sample, and the specific gravity of the urine is determined by the depth the urinometer sinks in the urine sample. The specific gravity value is read directly from the urinometer scale at the junction of the urine with the air. The urinometer method is cumbersome and suffers from the disadvantages of: a) requiring large volumes of urine test sample, b) a difficult and inaccurate reading of the urinometer scale, and c) unreliable assays because the urinometer is not regularly recalibrated.

Refractometry provides an indirect method of measuring the specific gravity of urine. The refractive index of urine is directly related to the number of dissolved particles in urine and, therefore, is directly related to the specific gravity of urine. Consequently, measurement of the refractive index of urine can be correlated to the specific gravity of urine. The refractometer method of determining urine specific gravity is desirable because specific gravity measurements are performed on as little as one drop of urine. However, the refractometer has the disadvantages of requiring daily calibration and not being amenable to home assays.

The falling drop method is another method of assaying for specific gravity which, like the urinometer, directly measures urine specific gravity. In this method, a drop of urine is introduced into each of a series of columns filled with solvent mixtures of increasing and known specific gravity. When the drop of urine comes to rest after its initial momentum has dissipated, and then neither rises nor falls, the specific gravity of the urine is determined to be identical to the specific gravity of the solvent mixture of that particular column. The falling drop method, however, is not widely used in routine urinalysis because of the lengthy time requirements in setting up such a assay and the inability of an individual to perform the assay at home.

The falling drop method described above also can be performed instrumentally. The instrument-based assay uses a specially designed column filled with a silicone oil having a controlled specific gravity and viscosity. The column is designed to measure the time required for a precisely measured drop of test sample to fall a distance defined by two optical gates (lamp-phototransistor pairs) mounted one above the other in a temperature-controlled column filled with a water-immiscible silicone oil of a slightly lower density than the test sample. The falling time is measured electronically and computed into specific gravity units. This specific gravity method is very precise, but the cost of the assay instrument and the degree of skill required to operate the instrument makes home testing for urine specific gravity impractical.

Not one of the above-described specific gravity assay methods is suited to performing specific gravity assays outside a medical office or laboratory. Consequently, reagent impregnated test strips were developed to enable an individual to perform specific gravity assays at home. In general, the test strip assay developed for specific gravity determinations is an indirect assay method, wherein the test strip changes color in response to the ionic strength of the urine sample. The ionic strength of a test sample is a measure of the type and amount of ions present in a test sample. The specific gravity of a test sample is proportional to test sample ionic strength. Therefore, by assaying for the ionic strength of a test sample, the specific gravity is determined indirectly and semiquantitatively by correlating the ionic strength of the test sample to the specific gravity of the test sample.

The present day specific gravity nest strips are sample pH dependent, and comprise a carrier matrix impregnated with a reagent composition including a polyelectrolyte, such as a partially neutralized poly(methyl vinyl ether/maleic acid); a chromogenic indicator, such as bromothymol blue; and suitable buffering agents. The reagent composition is sensitive to the number of ions, or electrolytes, in the test sample, such that the polyelectrolyte of the reagent composition undergoes an ion exchange, and releases hydrogen ions to the test sample in exchange for cations present in the test sample in an amount relative to take ionic strength of the urine sample.

Therefore, as the concentration of electrolytes in urine increases (high specific gravity), more cations are available to exchange with the hydrogen ions present on the polyelectrolyte of the reagent composition. The overall result is a release of hydrogen ions into the urine sample, and a resulting pH decrease of the urine sample that causes a color transition of the bromothymol blue chromogenic indicator from blue-green to green to yellow-green in response to increased specific gravity. The resulting color transition, indicating a pH change of the solution caused by increasing ionic strength, i.e., increasing specific gravity, is empirically and semiquantitatively related to the specific gravity of the urine sample.

For test strips utilizing the partially neutralized poly(methyl vinyl ether/maleic acid) polyelectrolyte and bromothymol blue indicator, assays for specific gravity are performed on aqueous test samples having a specific gravity of about 1.000 to about 1.030. A reading of 1.000, or a blue-green color, indicates that the urine has a very low specific gravity, as demonstrated by the lack of a color transition of the chromogenic indicator dye. A specific gravity reading of about 1.005 to about 1.030 is signified by color transitions, from blue-green through green to yellow-green, that serve as reliable indicators of increasing specific gravity.

It would be extremely advantageous to have a simple, trustworthy method of quantitatively assaying for urine specific gravity that allows visual differentiation of specific gravity values of about 1.000 to about 1.050. By providing a quantitative method of determining urine specific gravity in an easy to use form, such as a dip-and-read test strip, the urine assay can be performed by laboratory personnel to afford immediate test results. The specific gravity assay results can be interpreted in conjunction with assays for other urine constituents, such that a diagnosis can be made without having to wait for assay results and medical treatment can be commenced immediately. Furthermore, the test strip method can be performed by an individual at home to estimate the specific gravity of the urine and therefore to help monitor the success of the medical treatment the individual is undergoing.

As will be described more fully hereinafter, the method of the present invention is independent of test sample pH, and allows the fast and trustworthy assay for ionic strength or specific gravity of urine and other aqueous test samples by utilizing a test strip having a test pad that incorporates a reagent composition comprising: (1) a strong polyelectrolyte and (2) an indicator that is capable of binding with the polyelectrolyte and undergoing a spectral shift (i.e., is met&chromatic) and is sensitive to pH changes. The reagent composition is buffered at a pH of about 3 or less. For low to medium specific gravity test samples (i.e., less than about 1.015), the reagent composition undergoes a color transition in response only to the ionic strength, or ion concentration, of the test sample. The color transition is directly related to the ionic strength of the test sample. For high specific gravity test samples (i.e., about 1.015 or greater), the reagent composition undergoes a color transition in response to both the ionic strength and the buffer capacity of the test sample. As will be demonstrated more fully hereinafter, the reagent composition provides sufficient assay sensitivity to allow the quantitative determination of ionic strength and specific gravity of low through high specific gravity test samples.

Any method of assaying for the ionic strength or the specific gravity of urine or other aqueous test samples must yield trustworthy and reproducible results by utilizing a reagent composition that undergoes a color transition in response to the ionic strength and buffer capacity, or to the specific gravity, of the test sample, and not as a result of a competing chemical or physical interaction, such as a preferential interaction with another test sample component, like protein or glucose. Additionally, the method and composition utilized in the ionic strength or specific gravity assay should not adversely affect or interfere with the other test reagent pads that are present on multiple test pad strips.

In accordance with the present invention, the reagent composition incorporated into the carrier matrix provides sufficient sensitivity and color differentiation to assay for ionic strength, and therefore assay for specific gravity. The method is useful for measuring test sample specific gravity from about 1.000 to about 1.040. In addition, although dry phase nest strips have been used to assay for specific gravity, no dry phase test strip has incorporated a strong polyelectrolyte and an indicator that is capable of binding to the polyelectrolyte and that is sensitive to pH changes, buffered at a pH of about 3 or less, in an assay method for test sample ionic strength or specific gravity that is essentially independent of test sample pH. In addition, the assay method is intentionally designed to be essentially independent of the buffering capacity of a low to medium specific gravity test sample, but is sensitive to the buffering capacity of high specific gravity test samples, thereby improving the correlation of ionic strength to specific gravity and providing a more accurate assay for specific gravity.

Prior patents disclose the polyelectrolyte-dye ion exchange chemistry utilized in the present-day specific gravity assay of urine. For example, Falb et al. U.S. Pat. No. 4,318,709 and Stiso et al. U.S. Pat. No. 4,376,827 disclose a polyelectrolyte-dye technique used to assay for urine specific gravity. Each patent teaches utilizing polyelectrolyte-dye chemistry to determine the specific gravity of urine by monitoring the color transition of the dye.

The Falb et al. and Stiso et al. patents each disclose a composition and a method wherein the cations present in the test sample induce an ion exchange with the polyelectrolyte, thereby introducing hydrogen ions into the test sample. The change in hydrogen ion concentration, i.e., pH, is detected by a pH indicator. Accordingly, the previously disclosed methods are sensitive to the pH of the aqueous solution, and no direct interaction between the indicator dye and the polyelectrolyte occurs.

In addition, test sample buffer capacity interferes with the methods of Stiso et al. and Falb et al. because the polyelectrolyte-dye is buffered at a pH of about 6 to about 8 (which is within the urine pH range of about 5 to about 9). Test sample buffer capacity counteracts the introduction of hydrogen ions into the test sample by the polyelectrolyte, adversely affects the color transition, and thereby reduces the accuracy of the assay.

As used here and hereinafter, the term "metachromatic dye" is defined as a dye capable of undergoing a spectral shift upon binding to a polyelectrolyte, as opposed to a color transition due to a pH change. Accordingly, the term "metachromatic dye" encompasses: (1) dyes conventionally termed metachromatic which do not respond to changes in pH, i.e., "pH-insensitive metachromatic dyes" and (2) pH indicator dyes that bind to polyelectrolyte and undergo a color transition at a pH about 1 to 2 units below the $pK_a$ of the dye as a result of a polyelectrolyte-dye interaction as opposed to a pH change, i.e., "pH-sensitive metachromatic dyes". Such dyes are capable of exhibiting a color change due to metachromasia and a pH change.

The composition and method of the present invention differ from the Stiso et al. and Falb et al. patents in that an indicator, like a metachromatic dye, first binds to the polyelectrolyte. The metachromatic dye also can be sensitive to pH changes and undergo a color transition and thereby act as a pH indicator. Alternatively, if the metachromatic dye is not sensitive to pH changes, a separate pH indicator dye can be included in the composition. In addition, the composition is buffered at a pH of about 3 or less, and, preferably the strong polyelectrolyte is present in the acid form.

Upon contact between the reagent composition and a test sample that includes metal cations, such as urine, the metal cations compete for available binding sites on the polyelectrolyte and displace a number of the metachromatic dye molecules from the polyelectrolyte. As will be discussed in more detail hereinafter, upon release from the polyelectrolyte, the spectral properties of the metachromatic dye molecules change and a color transition results. The color transition is directly proportional to the amount of metachromatic dye released from the polyelectrolyte, which in turn is directly related to the ionic strength of the test sample. The color change can be correlated, quantitatively, to the ionic strength of the test sample; and the ionic strength of the test sample can be correlated, quantitatively, to the specific gravity of the test sample.

In addition, for test samples having a high specific gravity (e.g., about 1.015 or greater), the primary color transition attributed to test sample ionic strength is augmented by the effects of test sample buffer capacity, which cause a secondary color transition in the released metachromatic dye or the pH indicator dye. Accordingly, and in contrast to the Falb et al. and Stiso et al. disclosures, the present method is independent of test sample pH because the primary color transition results from a pH-independent displacement of the metachromatic indicator dye from a polyelectrolyte, like the acid form of a poly(vinyl sulfate). For test samples having a specific gravity of about 1.015 or greater, the accuracy of the method is improved by the secondary color transition attributed to a pH change resulting from the buffer capacity of the test sample.

In accordance with an important feature of the present invention, the indicator utilized in the method and composition of the present invention is capable of binding to the polyelectrolyte, and is able to respond to the buffer capacity of a test sample having a specific gravity of about 1.015 or greater, when the composition is buffered at a pH of about 3 or less. Accordingly, a single dye that exhibits both properties, or a combination of dyes, can be used as the indicator in the composition. Buffering the composition at a pH of about 3 or less ensures that displacement from the polyelectrolyte and a pH change due to test sample buffer capacity in a high specific gravity test sample will have similar or synergistic effects on the color transition of the indicator. This is contrary to the methods of Stiso et al. and Falb et al.

The present invention provides a composition and method for the accurate determination of ionic strength and specific gravity of urine and other aqueous test samples by utilizing an indicator that is sensitive to test sample ionic strength and buffer capacity, wherein the reagent composition is buffered at a pH of about 3 or less. European Patent Application 0 349 934 discloses a test strip and method of determining specific gravity or ionic strength of a sample utilizing a composition including a buffer, a complex former and a pH indicator dye. The complex former can be a crown ether, a cryptand, a podand or a multifunctional liquid. The method disclosed in the European Application is pH dependent, and utilizes a standard pH indicator dye, such as bromothymol blue or thymol blue. European Patent Application 0 349 934 does not teach or suggest a metachromatic dye or a polyelectrolyte utilized in the present invention.

Greyson et al. in U.S. Pat. No. 4,015,462 discloses a support matrix incorporating osmotically-friable microcapsules containing a fluid including a dye. A portion of the microcapsules bursts upon contact with a test sample of low osmolality. A resulting release of the dye-containing fluid causes a color transition that is correlated to the specific gravity. However, the difficult production of the microencapsulated-containing supporting matrix is a serious disadvantage of the Greyson et al. method.

In contrast to the prior art, and in contrast to the presently available commercial test strips, the method of the present invention provides a sensitive measurement of test sample ionic strength and specific gravity by utilizing a reagent composition including an indicator capable of responding to test sample ionic strength and buffer capacity, such as 2-[4-dimethylamino)styrl]-1-methylpyridinium iodide or quinaldine red, and a strong polyelectrolyte, like a poly(vinyl sulfate) or a poly(styrenesulfonate), in the acid form and buffered at a pH of about 3 or less, wherein the method is essentially independent of test sample pH. The present reagent composition undergoes a sufficient color transition upon contact with a test sample to provide an accurate ionic strength or specific gravity assay. The accuracy of assays for high specific gravity test samples is improved by a supplementary color transition attributed to test sample buffer capacity. Hence, new and unexpected results are achieved in the dry phase reagent strip assay of urine and other aqueous test samples for ionic strength or specific gravity.

SUMMARY OF THE INVENTION

In brief, the present invention is directed to a new and improved method and composition for determining the ionic strength or specific gravity of an aqueous test sample, and especially the ionic strength or specific gravity of a biological fluid, such as urine, perspiration, or serum. The method includes using a reagent composition capable of interacting with metal cations in a test sample to produce a detectable and measurable response that can be correlated to the ionic strength or specific gravity of the test sample. The response is essentially independent of the test sample pH. For home use, the reagent composition produces a visually detectable response. For laboratory use, the reagent composition produces a response that is detectable visually or instrumentally.

The method is suitable for dry phase assays, wherein the reagent composition is incorporated into a carrier matrix to provide a test pad of a test device. The carrier matrix of the test pad comprises a bibulous porous material, like filter paper, or a nonbibulous porous material, like a glass fiber or a permeable layer of a polymeric material. The reagent composition is homogeneously incorporated into the carrier matrix, and the carrier matrix then holds the reagent composition homogeneously throughout the carrier matrix in a known concentration while maintaining carrier matrix penetrability for the liquid test sample.

More particularly, the present invention is directed to a method of assaying for the ionic strength or specific gravity of urine and other biological or aqueous test samples by utilizing a new reagent composition. It has been demonstrated that employing a reagent composition including: (1) a metachromatic dye that also is sensitive to pH changes, or to a combination of a metachromatic dye and a pH indicator dye and (2) a strong polyelectrolyte, buffered at a pH of about 3 or less, provides sufficient sensitivity to test sample ionic strength, and a sufficient color differentiation between test samples of different specific gravity, to permit the accurate measurement of ionic strength or specific gravity. Surprisingly, the present method is essentially independent of test sample pH, and the accuracy of high specific gravity assays is improved by color transitions induced by a pH change attributed to the buffer capacity of the test sample.

In accordance with an important feature of the present invention, the specific gravity of aqueous test samples can be determined, quantitatively, between about 1.000 and about 1.040. By including either a metachromatic dye that also is sensitive to pH changes, or a combination of a metachromatic dye and a pH indicator dye, and a strong polyelectrolyte in a reagent composition buffered at a pH of about 3 or less, the assays are essentially independent of test sample pH. An improved assay sensitivity to high ionic strength and specific gravity is achieved by utilizing the present reagent composition because of the supplementary color transition attributed to the buffer capacity of the test sample. Accordingly, the present reagent composition allows a quantitative measurement of ionic strength or specific gravity of urine or other test samples.

Therefore, one aspect of the present invention is to provide a new method and composition for determining the ionic strength or specific gravity of an aqueous liquid. The new composition interacts with metal cations in an aqueous test sample to produce a visible change, such as a change in color of a test device, that is indicative of the ionic strength or the specific gravity of the test sample.

Another aspect of the present invention is to provide a method of assaying urine or other aqueous test samples having sufficient sensitivity and sufficient visual color resolution to allow differentiation between, and the measurement of, test sample ionic strengths.

Another aspect of the present invention is to provide a method of assaying urine or other aqueous zest samples utilizing a reagent composition capable of interacting with metal cations present in urine or other aqueous test samples, and undergoing a detectable and measurable color transition, independent of test sample pH, to establish the ionic strength or the specific gravity of the test sample.

Another aspect of the present invention is to provide a reagent composition that interacts with metal cations present in the test sample and undergoes a visually or instrumentally differentiable color transition, and also responds to the buffer capacity of high specific gravity test samples, to allow the quantitative determination of test sample specific gravity from about 1.000 to about 1.040.

Another aspect of the present invention is to provide a method of assaying for the ionic strength or specific gravity of a liquid test sample by incorporating a reagent composition into a dry phase detection device, wherein the reagent composition comprises: (a) an indicator comprising a dye that: (i) is metachromatic and sensitive to pH changes, or (ii) a combination of a metachromatic dye and a pH indicator dye; (b) a strong polyelectrolyte, like the acid form of a poly(vinyl sulfate) or a poly(styrenesulfonate); and (c) a suitable carrier, buffered at a pH of about 3 or less.

Still another aspect of the present invention is to provide a new and improved method of assaying for the ionic strength or specific gravity of an aqueous test sample by utilizing a test device including a carrier matrix having incorporated therein a reagent composition capable of interacting with metal cations present in the test sample and responding to the buffer capacity of high specific gravity test samples, wherein the carrier matrix comprises a bibulous matrix, like filter paper, or a nonbibulous matrix, like a glass fiber or a layer of a permeable polymeric material.

A further aspect of the present invention is to provide an improved dry phase test strip that incorporates a reagent composition comprising an indicator, and the acid form of a strong polyelectrolyte, buffered at a pH of about 3 or less, into the carrier matrix, and thereby provide an ionic strength or specific gravity assay in response to the ionic strength and buffer capacity of a test sample.

Another aspect of the present invention is to provide an improved specific gravity method assay of a test sample having a specific gravity of about 1.015 to about 1.040 by correlating the ionic strength and the buffer capacity of the test sample to specific gravity.

The above and other aspects and advantages and novel features of the present invention will become apparent from the following detailed description of the preferred embodiments.

DETAILED DESCRIPTION OF THE PREFERRED EMBODIMENTS

Figure 1:
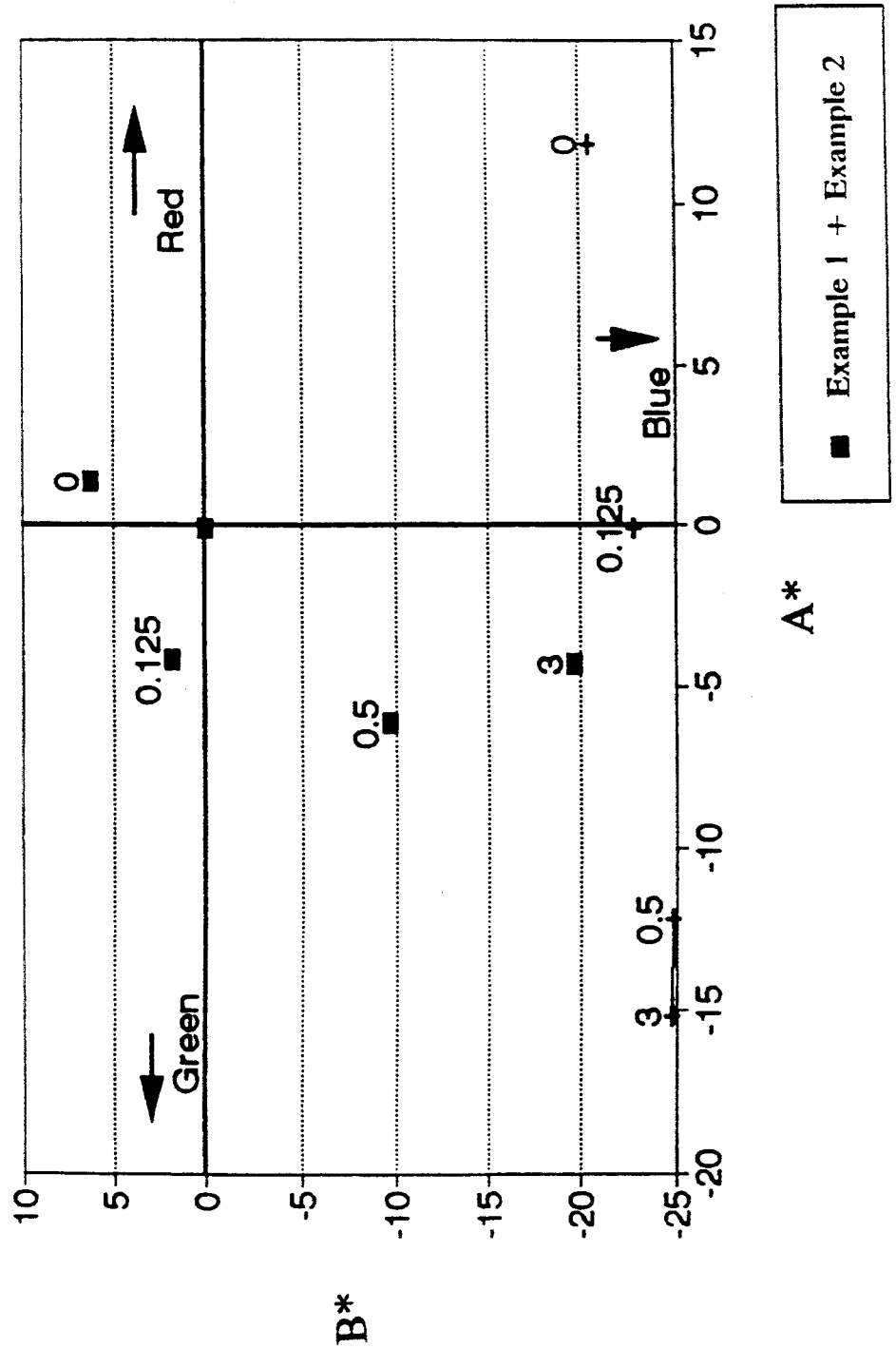
FIG. 1 is a two dimensional color space plot of A* vs. B*, illustrating the color transition of the reagent compositions of Examples 1 and 2 to varying concentrations of sodium chloride.

In accordance with the method of the present invention, the assay of aqueous test samples for ionic strength or specific gravity is accomplished by utilizing a reagent composition comprising: (a) an indicator comprising: (i) a dye that is metachromatic and sensitive to pH changes, or (ii) a combination of a metachromatic dye and a pH indicator dye, and (b) a strong polyelectrolyte, wherein the composition is buffered at about 3 or less. By employing a reagent composition including a sufficient amount of an indicator and of a strong polyelectrolyte, in the acid form, sufficient sensitivity and sufficient visual color differentiation between test samples of differing ionic strengths and buffer capacity are achieved. Surprisingly, the method is essentially independent of test sample pH, and of the buffer capacity of test samples having a specific gravity of less then about 1.015.

Accordingly, the accurate, reproducible ionic strength assay of aqueous test samples, independent of test sample pH, is provided. The composition and method also can be used to quantitatively determine test sample specific gravity because specific gravity can be correlated to ionic strength. Furthermore, the assay accuracy of high specific gravity test samples is enhanced by a response to the buffer capacity of the test sample. The accuracy of high specific gravity assays is enhanced by the color transition resulting from a pH change due to the buffer capacity of the test sample. The sensitivity and color resolution to test sample ionic strength and buffer capacity, and to specific gravity, afforded by the method of the present invention are especially useful in urine assays.

Present day commercial test strip assays measure specific gravities between about 1.000 and about 1.030, but buffer capacity of the test sample interferes in the assay because operating pH of the assay overlaps test sample pH. In addition, present day test strips are not capable of accurately assaying for ionic strength. However, the present composition and method allow an individual to test for ionic strength or for specific gravity without buffer capacity interference at home with a test strip.

The present invention also allows the quantitative assay of test sample specific gravity because specific gravity is correlated to ionic strength and, for high specific gravity test samples, to buffer capacity. The quantitative assay for urine specific gravity is clinically important because the urine specific gravity assay is interpreted in conjunction with assays for other urine analyses to assist in diagnosing a diseased state. The present invention is useful in assaying a urine sample having a specific gravity of about 1.000 to about 1.040, and provides improvements in assaying a urine sample having a specific gravity of about 1.015 to about 1.040. For urine specific gravities within the relatively normal range of about 1.010 to about 1.025, the method of the present invention still affords sufficient color differentiation and sufficient sensitivity to urine specific gravity. However, clinical benefits are realized in this normal specific gravity range by interpretation of the specific gravity assay in conjunction with urine assays for other analyses, such that all of the assays can provide information concerning an abnormal physiological state that must be investigated further.

It will become apparent that in addition to assaying urine, the method and composition of the present invention also can be used to determine the ionic strength or specific gravity of blood plasma and serum; and more generally, the ionic strength or specific gravity of many other physiological fluids, like perspiration, as well.

To achieve the full advantage of the present invention, the method and composition are employed in dry phase, test pad assays to determine the ionic strength or the specific gravity of urine or other aqueous test samples. A dry phase test strip, including a test pad comprising a carrier matrix incorporating a reagent composition of the present invention, allows the rapid, quantitative ionic strength or specific gravity assay of urine by visual means.

In particular, the present invention allows determination of ionic strength, or specific gravity, of a test sample by a visual color change of a test pad on a test strip. The test strip includes a test pad comprising an inert carrier matrix incorporating a reagent composition comprising a sufficient amount of a suitable indicator, and a strong polyelectrolyte, buffered at a pH of about 3 or less. The ionic strength is determined from the color transition of the reagent composition. For high specific gravity test samples, the primary color transition is supplemented by a secondary color transition resulting from a pH change. The pH change is attributable to the buffer capacity of the test sample. Test sample specific gravity is determined by quantitatively correlating the total color transition resulting from test sample ionic strength and buffer capacity to test sample specific gravity.

The present composition and method allow the rapid colorimetric determination of the ionic strength or specific gravity of a test sample. Previous specific gravity assay methods employed indicator dyes that are sensitive to, and therefore measured, only solution pH. The present method utilizes a dye that is both metachromatic and sensitive to pH changes, or to a combination of a metachromatic dye and a pH indicator dye, and a strong polyelectrolyte, but is essentially independent of the pH normally encountered in urine samples, e.g., pH of about 5 to about 9. If the indicator is a metachromatic dye that also can act as a pH indicator, i.e., changes color in response to a pH change, the reagent composition is buffered at sufficiently low pH such that the dye does not change color as a result of test sample pH.

For a test sample having a low to medium specific gravity (e.g., less than about 1.015), the pH of the test pad remains constant or may decrease slightly. However, for a test sample having a high ionic strength or a high specific gravity (e.g., about 1.015 or greater), the buffer capacity of the test sample is such that the pH of the test strip rises, thereby deprotonating the indicator and causing a color transition. This pH-change induced color transition enhances the overall color transition. This enhanced overall color transition provides a more accurate specific gravity assay of high specific gravity urine samples. The buffer capacity of a low to medium specific gravity test sample does not contribute to the overall color transition.

The pH indicator dyes used in present day specific gravity assays undergo color transitions due to a test pad pH change in the range of pH about 6 to about 8. The color transition results from an ion exchange between the polyelectrolyte and cations present in the test sample. The phenomena is fully described in Falb et al. U.S. Pat. No. 4,318,709 and Stiso et al. U.S. Pat. No. 4,376,827, wherein the various dyes, the polyelectrolytes and the buffers required to observe the pH change are disclosed. The Falb et al. and Stiso et al. patents basically describe the present day dry phase test strips employed to assay for the specific gravity of urine. These present day test strips generally include: (a) an indicator dye that normally undergoes a color transition in the neutral pH range of about 6 to about 8, such as bromothymol blue; (b) a partially neutralized polyelectrolyte; and (c) a buffer to maintain an operating pH of about 5.5 or greater, and typically about 6 to about 8.

In accordance with the methods of Stiso et al. and Falb et al., as the ionic strength of the urine increases, hydrogen ions are released into the solution due to an ion exchange between the cations in the test sample and the polyelectrolyte. The overall result is a drop in pH of the solution, and the bromothymol blue indicator changes color from blue-green to green to yellow-green in response to the pH change caused by increasing ionic strength. The increase in ionic strength of an aqueous test sample is directly related to an increase in specific gravity; the color transition of the dye therefore is empirically related to specific gravity values. This present day method allows specific gravities to be determined to within about 0.005. The present day method suffers from the disadvantage of color transition instability, wherein the color transition fades over a time period of minutes, and of interferences attributed to test sample buffer capacity. Accordingly, assay results are technique dependent and have an inherent inaccuracy.

In accordance with the present method, assays for the ionic strength or specific gravity of an aqueous test sample are determined by examining a dry phase test strip for a visual color change after the test strip contacts a test sample. The test strip comprises a test pad, said test pad including a carrier matrix incorporating a reagent composition comprising a strong polyelectrolyte and a suitable indicator. The indicator comprises a metachromatic dye that also is sensitive to a change in pH, or can be combination of a metachromatic dye and a pH indicator dye, or combinations thereof. The metachromatic dye combined with the pH indicator can be either a pH-sensitive or pH-insensitive metachromatic dye. Preferably, the indicator comprises a combination of at least two dyes, wherein at least one dye is responsive to a change in pH. In contrast to previous methods which utilized dyes that sensed the bulk pH of the solution in the range of about 6 to about 8, the present method is essentially independent of normally-encountered pH values and the reagent composition is buffered at a pH of about 3 or less.

The above-discussed Falb et al. and Stiso et al. patents disclose the determination of ionic strength by inducing changes in the pH of the solution by an ion exchange with a polyelectrolyte. This pH change is measured by a pH indicator dye. The methods disclosed by Stiso et al. and Falb et al. are sensitive to the pH of the aqueous solution; no direct interaction between the pH indicator dye and the polyelectrolyte occurs; and a high urine pH (i.e., above 6.5) must be adjusted to obtain an accurate specific gravity assay. The methods discussed by Stiso et al. and Falb et al. also are sensitive to normal fluctuations in test strip manufacturing. For example, variations in carrier materials and in drying conditions of the test strip, and lot-to-lot differences in a polyelectrolyte, each can influence the final surface pH of the test strip. Variances in the final surface pH of the test strip result in inaccurate ionic strength or specific gravity measurements because the test strip becomes either more or less sensitive to pH changes.

The present invention differs from the methods disclosed by Stiso et al. and Falb et al. in that the present method is essentially pH insensitive within the normal urine pH range (e.g., 5 to 9). This pH independence eliminates the need for specific gravity corrections of urine samples having a high pH. The present pH independent method also avoids the above-described manufacturing problems associated with the present pH-dependent test strips.

In accordance with the present invention, first a direct interaction (i.e., binding) between a metachromatic dye and a strong polyelectrolyte occurs. Then, a portion of the metachromatic dye molecules is released from the polyelectrolyte after contact with the test sample. The released dye molecules undergo a spectral shift and, accordingly, a primary color transition occurs. The primary color transition is essentially independent of test sample pH and is directly proportional to test sample ionic strength. The primary color transition thus can be correlated to test sample specific gravity to provide a quantitative specific gravity assay.

If the metachromatic dye also is sensitive and responds to pH changes, the released metachromatic dye can undergo a secondary color transition due to a pH change induced by test sample buffer capacity. If the metachromatic dye is insensitive to pH changes, a pH indicator dye is included in the reagent composition to provide a secondary color transition attributable to test sample buffer capacity. A pH indicator dye, or a metachromatic dye that changes color in response to a pH change, can be utilized because the reagent composition is buffered at a pH of about 3 or less, thereby preventing a color change due to test sample pH and allowing a color change resulting from release of the indicator from the polyelectrolyte.

For test samples having a high ionic strength and specific gravity (i.e., about 1.015 or greater), a portion of the pH-sensitive dye molecules that are free in solution, are deprotonated due to the buffer capacity of the test sample. Deprotonation of the pH-sensitive dye molecules (either a metachromatic dye or a pH indicator dye) causes a secondary color transition that augments the primary color transition resulting from the release of metachromatic dye molecules from the polyelectrolyte. This secondary color change therefore factors in the effects of test sample buffer capacity, and, in conjunction with the measurement of test sample ionic strength, allows the more accurate determination of a urine specific gravity of about 1.015 or greater.

The publication, "Interaction Between Cationic Dyes and Polyelectrolytes", by V. Vitagliano, *Chemical and Biological Applications of Relaxation Spectrometry*, E. Wyn-Jones, ed., D. Reidel Publishing Co., Boston, Mass. (1975), pp. 437–466, describes the interaction between a cationic dye, like a metachromatic dye, and a polyelectrolyte having negatively-charged sites, like a poly(styrenesulfonate). It is known that the interaction, or binding, between a cationic dye molecule and a negatively-charged site of the polyelectrolyte is influenced by the ionic strength of a solution, with the binding between the dye molecules and the polyelectrolyte decreasing as solution ionic strength increases. The present invention utilizes this property in a pH independent method and device to assay an aqueous test sample for ionic strength, and in conjunction with test sample buffer capacity, for specific gravity.

In particular, the present invention utilizes a reagent composition comprising: (1) a strong polyelectrolyte in the acid form, and (2) an indicator comprising (i) a metachromatic dye capable of responding to pH changes, or (ii) a combination of a metachromatic dye and a pH indicator dye, buffered at a pH of about 3 or less, to achieve maximum sensitivity to test sample ionic strength or specific gravity, independent of test sample pH. The metachromatic dye binds to a negatively-charged site on the polyelectrolyte. This binding of the metachromatic dye to the polyelectrolyte induces a spectral shift in the metachromatic dye due to dye molecules being in proximity to one another.

In particular, dyes that exhibit metachromasia are included in the present reagent composition because metachromatic dyes undergo a color change upon binding to, or release from, either a natural or a synthetic polyelectrolyte. Metachromasia is common in dyes having an electric charge partially delocalized into the chromophore group of the dye. As the metachromatic dye molecules bind to the negatively-charged sites on the polyelectrolyte, the metachromatic dye molecules interact with one another, thereby inducing a change in the spectral properties of the metachromatic dye, said change being observable as a color transition.

Metal cations affect the binding of the metachromatic dye to the polyelectrolyte because the metal cations successfully compete with the metachromatic dye for the available negatively-charged sites on the polyelectrolyte. Therefore, as the ion concentration of a solution increases (i.e., ionic strength or specific gravity increases), a greater amount of the metachromatic dye is released from the polyelectrolyte because the metal cations preferentially bind to the polyelectrolyte at the expense of the metachromatic dye. The release of metachromatic dye molecules from the polyelectrolyte into the solution results in a color transition because the spectral properties of the metachromatic dye return to the normal solution state spectral properties of the unbound dye. Therefore, the amount of metachromatic dye released from the polyelectrolyte, as determined by the color transition, can be correlated to test sample ionic strength and indirectly to specific gravity.

This polyelectrolyte-metachromatic dye interaction and color transition is sufficient to accurately determine low to medium specific gravities of about 1.000 up to about 1.015. However, in addition, as the ionic strength of a test sample increases, the buffer capacity of the test sample also can increase. This ionic strength-buffer capacity relationship is especially strong in urine samples, and particularly in urine samples having a specific gravity of about 1.015 or greater. In such high specific gravity urine samples, the corresponding high buffer capacity adversely affects the correlation of ionic strength to specific gravity, and accordingly adversely affects specific gravity assay accuracy. For low to medium specific gravity urine samples, the relatively low buffer capacity does not adversely affect the correlation of ionic strength to specific gravity correlation.

Therefore, in accordance with an important feature of the present invention, the reagent composition includes an indicator that, in addition to exhibiting metachromasia to provide a primary color transition, can respond to a pH change attributed to test sample buffer capacity, and undergo a secondary color transition to supplement the primary color transition resulting from dye release from the polyelectrolyte. As will be explained more fully hereinafter, the secondary color transition does not occur in urine samples having a specific gravity of less than about 1.015, but occurs only for urine samples having a specific gravity of about 1.015 or greater. A urine specific gravity above about 1.015 can have sufficient buffering capacity to overcome the buffering capacity of the strong electrolyte. The secondary color transition enhances a primary metachromatic color transition and allows a more accurate correlation of the total color transition, which is based on ionic strength and buffer capacity, to urine specific gravity.

The method of the present invention therefore utilizes the color transition that occurs: (1) primarily as a result of metal cations present in the test sample causing a release of a metachromatic dye bound to a polyelectrolyte, and (2) secondarily as a result of buffer capacity causing a chromogenic change in a pH-sensitive metachromatic dye or an additional pH indicator dye because of a test strip pH change. Including a suitable indicator and a strong polyelectrolyte in a reagent composition buffered at a pH of about 3 or less allows the ionic strength of a test liquid to be accurately and reliably measured. In accordance with an important feature of the present invention, the release of a metachromatic dye from the polyelectrolyte by metal cations present in the test sample provides a differentiable color transition that can be correlated to test samples having a different ionic strength. The ionic strength can be correlated quantitatively to test liquid specific gravity. In high specific gravity test samples, a dye that is also sensitive to pH changes undergoes a secondary color transition in response to test sample buffer capacity. Accordingly, a more accurate measurement of test sample specific gravity is achieved because of improved assay sensitivity which accounts for buffer capacity and because of improved color resolution between test samples of different ionic strength.

Therefore, the reagent composition of the present invention comprises: (a) an indicator comprising (i) a metachromatic dye that is responsive to pH changes,. (ii) a combination of a metachromatic dye and a pH indicator dye, or (iii) mixtures thereof; (b) a strong polyelectrolyte, preferably in the acid form; and (c) a suitable carrier. The reagent composition is buffered at a pH of about 3 or less, and is used in a method, such as in a dry phase test strip method, to assay a test sample, like urine, for ionic strength or specific gravity. The pH-sensitive metachromatic dye and the pH indicator respond to pH changes at pH about 4 or less.

The indicator utilized in the present invention comprises (i) a metachromatic dye that is sensitive to pH changes, i.e., a pH indicator dye that exhibits metachromasia, (ii) a combination of a metachromatic dye and a pH indicator dye, or (iii) mixture thereof, as long as a dye that is sensitive (i.e., responds) to pH changes is present in the assay of test samples having a specific gravity of about 1.015 or greater. Metachromatic dyes are capable of binding to negatively-charged sites on naturally-occurring and synthetic polyelectrolytes. Therefore, the metachromatic dye often is a cationic compound. The visual spectrum of metachromatic dyes change when a monomeric form of the dye binds to a polyelectrolyte. Therefore, a solution including a metachromatic dye bound to a polyelectrolyte undergoes a color change when the metachromatic dye molecules are released from the polyelectrolyte. Metal cations release metachromatic dye molecules bound to the polyelectrolyte because the metal cations preferentially compete with the metachromatic dye for the available negatively-charged sites on the polyelectrolyte.

In general, the metachromatic dye can be essentially any dye, preferably a cationic dye, that is capable of delocalizing a positive charge into the chromophore group. Such dyes, after binding to a negatively-charged site of a polyelectrolyte, undergo a primary color transition upon release from the polyelectrolyte due to the presence metal cations, like sodium or potassium. The degree and intensity of the primary color transition are directly related to the concentration of metal cations in the test sample; and the concentration of the metal cations is directly related to the ionic strength of the test sample. Therefore, the degree and intensity of the primary color transition can be correlated to the ionic strength, and in turn the specific gravity, of the test sample.

If the metachromatic dye also is capable of undergoing a color transition in response to a pH change, no other dye is necessary in the reagent composition. If the metachromatic dye is insensitive to a pH change, then a pH indicator dye or a pH-sensitive metachromatic dye is included in the composition to provide a secondary color transition that is attributable to buffer capacity of a high specific gravity test sample. The degree and intensity of the secondary color transition are directly proportional to the change in pH; and the change in pH is directly related to buffer capacity and in turn to specific gravity. Therefore, a combination of responses to ionic strength and buffer capacity provides a more accurate specific gravity assay.

The particular dye or combination of dyes selected as the indicator of the reagent composition can be determined by those skilled in the art of designing test kits in order to produce a specific gravity assay having maximum visual color resolution and maximum sensitivity. A metachromatic dye or pH indicator dye included in the present reagent composition can be prepared by methods well known to persons skilled in the art. Furthermore, several metachromatic and pH indicator dye compounds useful in the method of the present invention are well known dyes that presently are available commercially.

The indicator is present in the reagent composition at a concentration of about 5 to about 100 mM (millimolar, or millimoles per liter), and preferably about 10 to about 80 mM. To achieve the full advantage of the present invention, the indicator is present in the reagent composition at a concentration of about 15 to about 60 mM.

The indicator comprises: (i) a metachromatic dye that is responsive to pH changes, (ii) a combination of a pH-insensitive or pH-sensitive metachromatic dye and a pH indicator dye, or (iii) a mixture thereof, as long as the indicator comprises a dye that undergoes a detectable spectral shift when metal cations cause release of the bound dye from the polyelectrolyte. The indicator therefore comprises a dye that not only exhibits metachromasia, but also is capable of responding, chromogenically, to a pH change attributed to the buffer capacity of a high specific gravity test sample. As will be demonstrated in detail hereinafter, to achieve the full advantage of the present invention, the indicator of the reagent composition comprises a first and a second pH-sensitive dye, wherein at least one dye is metachromatic, and wherein the second pH-sensitive dye has a $pK_a$ (acid dissociation constant) about one to about two units greater than the $pK_a$ of the first pH-sensitive dye.

Examples of dyes that bind to a polyelectrolyte, then are released from the polyelectrolyte due to the presence of metal cations to undergo a color change (i.e., exhibit metachromasia), and that respond to changes in pH at about 4 or less, include, but are not limited to, neutral red, basic fuchsin, new fuschin, benzopurpurin, quinaldine red, pinacyanol bromide, pinacyanol chloride, 2-[4-(dimethylamino)styrl]-1-methylquinolium iodide, 2-[4-(dimethylamino)styrl]-1-methypyridinium iodide, stains-all and crystal violet.

Examples of dyes that exhibit metachromasia and do not respond to pH changes include, but are not limited to, thionin, astrazon orange, astrazon blue, toluidine blue, methylene blue, acridine orange, pyronine-G, proflavine, azure A, phloxine B, cresyl violet, safranine O, thioflavin T, fast red AL, methylene green, rhodamine B, rhodamine 6G, azure B, indoine blue, brilliant cresyl blue, 4',6-diamidino-2-phenylindole dihydrochloride hydrate, acridine yellow, acriflavine, pyronin-Y, pyronin-B, meldola's blue, nile blue, nile red, new methylene blue, methyl violet, pinacryptol yellow and methyl green.

Examples of dyes that are sensitive only to pH changes at a pH of about 4 or less include, but are not limited to, victoria blue, brilliant green, ethyl violet, malachite green oxalate, metanil yellow, xylenol blue, methyl violet 2B, benzyl orange, bromphenol red, bromocresol green, thymol blue, and m-cresolsulfonephthalein. Any pH indicator dye capable of undergoing a color transition at pH of about 4 or less can be used in the present invention.

In accordance with an important feature of the present invention, if a pH indicator dye is used in conjunction with a pH-sensitive or pH-insensitive metachromatic dye, the color transition of the pH indicator dye should be different from the color transition of the metachromatic dye to provide a more spectacular and differentiable color transition. For example, if the metachromatic dye has a color change from colorless to red, the pH indicator dye preferably has a different color transition, such as from colorless to yellow. Then the resulting color transition for increasing pH is from colorless to red to red-orange.

The reagent composition also includes about 0.5% to about 4%, and preferably about 1% to about 3%, by weight, of a strong polyelectrolyte. To achieve the full advantage of the present invention, the reagent composition includes about 1% to about 2.5%, by weight, of the polyelectrolyte. The strong polyelectrolyte is present in the acid form and in a sufficiently high amount to buffer the reagent composition at a pH of about 3 or less, preferably at a pH of about 2 or less, and to achieve the full advantage of the present invention, at a pH of about 1.5 to about 2. This relatively high amount of a strong polyelectrolyte also is sufficient to effectively bind the metachromatic dye.

The polyelectrolyte is a strong polyelectrolyte, such as for example, but not limited to, a poly(vinyl sulfate), a poly(vinyl sulfonic acid), a poly(styrenesulfonic acid), poly(2-acrylamido-2-methyl-1-propanesulfonic acid), and mixtures thereof. The polyelectrolyte is included in the reagent composition in the acid form. Such strong polyelectrolytes sufficiently ionize in aqueous solution to provide a sufficient number of negatively-charged sites for binding to the metachromatic indicator dye and to provide a buffered pH of about 3 or less.

The molecular weight of the polyelectrolyte is not particularly critical. The interaction between the metachromatic dye and the strong polyelectrolyte is related to the concentration of negatively-charged moieties present in the composition, not to the molecular weight of the polyelectrolyte. Therefore, a critical aspect of the polyelectrolyte concentration is the presence of a sufficient amount of negatively-charged monomeric subunits to interact and bind with the indicator dye.

As previously described, in aqueous solution, a metachromatic dye binds to the strong polyelectrolyte to provide a solution having a color different from an aqueous solution including the monomeric metachromatic dye. If metal cations are present, the metal cations preferentially compete for the available negatively-charged binding sites on the strong polyelectrolyte, thereby releasing the metachromatic dye to the solution. The metachromatic dye then undergoes a color transition. The color transition is proportional to the amount of dye released from the polyelectrolyte. The color transition is correlated to the amount of metal cations in the solution (i.e., the ionic strength), which in turn can be correlated to the specific gravity of the solution.

For solutions having a high ionic strength and high buffer capacity, like a high specific gravity urine sample, the mere correlation between ionic strength and specific gravity is poor. Accordingly, for high specific gravity test samples, the buffer capacity also is measured to provide, in conjunction with the ionic strength determination, an accurate assay for test sample specific gravity.

In particular, in high specific gravity test samples, the metachromatic dye released from the polyelectrolyte into solution undergoes a primary color transition in response to metal cations in the test sample. If the metachromatic dye also is sensitive to pH changes, the dye undergoes a secondary color transition that is attributable to the buffer capacity of the test sample. If the metachromatic dye is not sensitive to pH changes, then a dye that is sensitive to pH changes, such as a pH indicator dye or pH-sensitive metachromatic dye, is included in the reagent composition to undergo a secondary color transition attributable to buffer capacity. This secondary color transition is in addition to the primary metachromatic color transition resulting from release of the metachromatic dye from the polyelectrolyte, and provides a more accurate assay for specific gravity by measuring ionic strength and buffer capacity.

In accordance with an important feature of the present invention, the present method is essentially independent of test sample pH, and especially over the pH range normally encountered in urine samples (e.g., a pH of about 5 to about 9) because the total color transition is proportional to: (1) the amount of metachromatic dye released from the polyelectrolyte, which is dependent only on the concentration of metal cations in the solution, and 2) the buffer capacity of the test sample.

Optionally, a buffer also can be included in the reagent composition. Typically, the acid form of the strong polyelectrolyte, like polystyrenesulfonic acid, effectively buffers the reagent composition to a pH of about 3 or less. Accordingly, no additional buffer is necessary. In addition, and if desired, a buffer having a $pK_a$ similar to the $pK_a$ of the polyelectrolyte, i.e., within about two $pK_a$ units, can be included in the reagent composition.

It is important to buffer the reagent composition with the strong electrolyte or an independently.-added buffer because pH shifts attributed to test sample buffer capacity then are observed only for high specific gravity test samples. The buffer capacity of low to medium specific gravity urines has no effect on the assay and does not contribute to the total color transition.

This difference is important because the ionic strength of low to medium specific gravity urine correlates well to specific gravity, whereas the ionic strength of high specific gravity urine does not correlate well to specific gravity. Therefore, a secondary color transition due to a pH change attributed to buffer capacity enhances the primary metachromatic dye color transition and improves the ionic strength-specific gravity correlation at a high specific gravity. For low to medium specific gravity urines, wherein ionic strength correlates well to specific gravity, an enhanced primary color transition is not necessary.

Any of various types of buffers having a $pK_a$ of about 5 or less can be used in the reagent composition of the present invention to provide a desired buffered pH of about 3 or less. The amount of buffer included in the reagent composition depends upon the nature of the indicator and strong polyelectrolyte present in the reagent composition. The concentration of the buffer usually is 0 to about 600 mM, and preferably 0 to about 300 mM. The particular buffer used in the reagent composition also depends upon, and varies with, the strong polyelectrolyte included in the reagent composition. For optimum assay results, the pH of the reagent composition preferably is maintained an a pH value of about 2 or less. To achieve the full advantage of the present invention, the strong polyelectrolyte and/or buffer maintains the pH of the reagent composition at about 1.5 to about 2.

If the indicator is a metachromatic dye that also is capable of changing color in response to a change in pH, i.e., is sensitive to a pH change and can act as a pH indicator, a single indicator can be included in the reagent composition for the assay of urine having a specific gravity of about 1.000 to about 1.040. If the indicator dye is a metachromatic dye that does not change color in response to a change in pH, the reagent composition provides an accurate specific gravity assay for to low medium specific gravity urines. However, the assay of a high specific gravity urine would be semiquantitative due to a reduced correlation of ionic strength to specific gravity. The specific gravity assay for a high specific gravity assay urine can be made more accurate by incorporating a second dye into the composition, wherein the second dye is capable of changing color in response to a change in pH attributable to the buffer capacity of the test sample.

Exemplary buffers include, but are not limited to, glycine; lysine; citraconic acid; sarcosine; phosphonic acid; amino acid buffers; trichloracetate; sulfosalicylate; phosphate; tartarate; citrate; succinate; maleic acid; 2,2-bis(hydroxymethyl)-2,2',2''-nitrilotriethanol; 3,3-dimethylglutaric acid; and other suitable buffers having a $pK_a$ of about 5 or less as are well known in the art, or combinations thereof.

In addition to the indicator and the strong polyelectrolyte, other optional ingredients, in addition to the buffer, that do not materially alter the nature or the function of the essential ingredients, and that do not interfere with the assay for specific gravity or ionic strength, also can be included in the reagent composition. For example, the reagent composition optionally can include a compound to improve the wetting of the test pad of the test device by the test sample. This compound usually is a nonionic surfactant. A nonionic surfactant, such as an octoxynol, a nonoxynol or an ethoxylated fatty alcohol, is the preferred surfactant. The nonionic surfactant is included in the indicator reagent composition in a concentration of 0 to about 200 mM, and preferably in a concentration of 50 to about 200 mM.

The reagent composition also can include a polymeric material that improves the stability and uniformity of the color transition of the test device. Suitable polymeric materials include, but are not limited to, polyvinylpyrrolidone, polyvinyl alcohol, gum arabic, gelatin, algin, carrageenan, casein, albumin, methyl cellulose and similar natural and synthetic polymeric materials. The preferred polymeric material is a polyvinylpyrrolidone of average molecular weight 40,000 and available commercially from GAF Corp., New York, N.Y. The polymeric material generally is included in the reagent composition in an amount of 0% to about 5%, and preferably 0% to about 4%, by total weight of the reagent composition.

In addition, the reagent composition also can include a chelating agent in order to reduce the number of metal cations in solution capable of competing with the metachromatic dye for the negatively-charged sites on the polyelectrolyte. A more differential color transition between test samples having a high concentration of metal cations, i.e., electrolytes, therefore results.

The optional chelating agent utilized in the present invention is not particularly limited. However, an organic chelating agent, like a chelating dicarboxylic or polycarboxylic acid, or a polycarboxyalkylamine chelating agent, such as ethylenediaminetetraacetic acid, is most preferably employed. Other classes of useful chelating agents include, but are not limited to, a polyhydroxy compound, like sorbitol; a lignosulfonate; a glucoheptonate; dimethylglyoxime; salicylate complexes, like bissalicylaldehydeethylenediimine; dithionate derivatives; polyethyleneamines, like triethyleneamine; a 2,4-pentanedione derivative; a dipyridine derivative; triethylenepyridine amine; a polypeptide containing cysteine, glycine or histidine; a proline derivative; a thiocrown ether, like 1,4,8,11,22,25-octathiacyclooctosane; a triphenylphosphine; or combinations thereof.

Particular examples of chelating agents useful in the reagent composition of the present invention include, but are not limited to, tartaric acid, oxalic acid, malonic acid, succinic acid, citric acid, ethylenediaminetetraacetic acid (EDTA), gluconic acid, N-(hydroxyethyl)ethylenediaminetriacetic acid (HEDTA), nitrilotriacetic acid (NTA), diethylenetriaminepentaacetic acid (DTPA), aminotris(methylene phosphoric acid), hydroxyethylidene diphosphonic acid, hexamethylenediaminetetra(methylene phosphonate), ethylenediaminediacetic acid (EDDA), iminodiacetic acid (IDA), nitrilopropionic acid (NTP), hydroxyethyliminodiacetic acid (HIDA) and 1-hydroxyethane-1,1-diphosphonic acid; or combinations thereof.

The chelating agent can be added to the reagent composition in the free acid form, or in the form of a water-soluble salt, such as the sodium, potassium, lithium, ammonium, alkyl-substituted ammonium or hydroxyalkyl-substituted ammonium salt. The chelating agent is included in the reagent composition in a concentration of 0 to about 5 mM, and preferably of 0 to about 4 mM.

The carrier for the ingredients included in the reagent composition is water, a water miscible alcohol or a mixture thereof. Suitable water-miscible alcohols are, for example, but not limited to, methanol, ethanol, isopropyl alcohol and combinations thereof. However, because of the limited water or alcohol solubility of particular ingredients included in the indicator reagent composition, other organic solvents such as ethylene glycol, propylene glycol, acetone, dimethylformamide, dimethylsulfoxide, acetonitrile, ethyl acetate and similar solvents can be included in the carrier. The selection of a suitable organic solvent or solvents, in addition to water and alcohols, to include in the carrier of the reagent composition is within the capability of those skilled in the art of designing diagnostic assays.

The amount of organic solvent other than an alcohol present in the indicator reagent composition generally is 0% to about 50%, and preferably 0% to about 10%, by weight of the carrier. A carrier comprising water and an alcohol, like methanol or ethanol, is especially preferred because a carrier matrix impregnated with the reagent composition can be dried within a few to several minutes. In addition, the presence of an alcohol helps prevent precipitation of the indicator by the polyelectrolyte.

As previously described, the reagent composition undergoes a color transition upon contact with a test sample in response to test sample ionic strength, and in some cases to test sample buffer capacity, to provide an assay for test sample ionic strength or test sample specific gravity. The intensity and degree of the color transition are used to quantitatively determine the ionic strength or specific gravity of the test sample. In accordance with an important feature of the present invention, a reagent composition of the present invention provides a sufficiently resolved and differentiated color transition such that the ionic strength or specific gravity of a test sample can be measured and accurately determined without the use of color-measuring instruments, such as spectrophotometers or colorimeters. However, if desired, such color-measuring instruments can be used to measure the difference in color degree and intensity between the test sample and a solution having a known ionic strength or specific gravity. Because ionic strength and buffer capacity are directly proportional to specific gravity, the color transition can be correlated to test sample specific gravity.

The intensity and degree of the color transition are used to determine the ionic strength or specific gravity of the test sample by comparing or correlating the color produced by the test sample to colors produced by solutions having a known ionic strength or a known specific gravity. In accordance with an important feature of the present invention, the reagent composition provides a sufficiently resolved and differentiated color transition such that the ionic strength, or the specific gravity, of the test sample can be measured without the use of color-measuring instruments.

Accordingly, the method of the present invention improves the accuracy and reliability of the quantitative ionic strength or specific gravity assay, and also increases physician confidence in the ionic strength or specific gravity assay. Because of the large number of urine assays for specific gravity being performed at home by untrained individuals, as opposed to trained physicians or technicians in the laboratory, it is imperative to provide a fast and reliable assay method for the specific gravity of urine and serum that can be used in conjunction with assays for other urine constituents.

Conventionally, assays for specific gravity have been conducted at an essentially neutral pH using a pH indicator dye that undergoes a color transition at an essentially neutral pH in response to an ion exchange between cations in solution and the acidic hydrogen atoms of a polyelectrolyte. The pH indicator dye therefore is actually sensing the pH of the solution. In accordance with the method and composition of the present invention, test sample specific gravity is determined quantitatively by the color transition resulting from metal cations present in the test sample releasing a bound metachromatic dye from a strong polyelectrolyte, which in turn causes a spectral shift in the dye. The metachromatic dye exhibits a different color spectrum in solution when bound to a polyelectrolyte, as opposed to the color spectrum exhibited when the metachromatic dye is in solution in the free state. Therefore, a color transition results when the metachromatic dye is released from the polyelectrolyte due to the presence of metal cations in the test sample. Such a color transition is essentially independent of test sample pH, because the color transition is related only to the color exhibited by the metachromatic indicator dye in its bound and free states and to the amount of metachromatic dye released from the polyelectrolyte. The degree and intensity of the color transition are directly related to the ionic strength, and therefore to the specific gravity, of the test sample.

The reagent composition is sufficiently buffered at a pH of about 3 or less such that the buffer capacity of low to medium specific gravity test samples does not affect the color transition of the indicator. However, in addition to the primary metachromatic color transition, the indicator can undergo a secondary color transition in response to a pH change attributable to the buffer capacity of a high specific gravity test sample, thereby improving the correlation between test sample ionic strength and specific gravity in a high specific gravity test sample.

To demonstrate the new and unexpected results achieved by the method and composition of the present invention, reagent compositions, including a strong polyelectrolyte and a suitable indicator, were prepared, then used in a dry phase assay for the specific gravity of a test sample. It has been demonstrated that if a sufficient amount of the acid form of the strong polyelectrolyte is included in the reagent composition, an additional buffer is not required because the polyelectrolyte provides a buffered pH of about 3 or less.

As a demonstration, the aqueous solution of a metachromatic dye (toluidine blue) and a salt form of a polyelectrolyte (potassium poly(vinyl sulfate)) is red-violet in color and, after incorporation into a suitable carrier matrix, like filter paper, changes color ranging from red-violet to sky blue after contact and interaction with test samples having an increasing ionic strength or specific gravity. As a result, a reagent composition including a sufficient amount of a metachromatic indicator dye, like toluidine blue; and a strong polyelectrolyte, like potassium poly(vinyl sulfate) (KPVS), after incorporation into a suitable carrier matrix, produced the color transitions summarized in TABLE I upon contact and interaction with standard solutions including metal cations and having the following specific gravities:

TABLE I

COLOR TRANSITION OF A REAGENT COMPOSITION INCLUDING TOLUIDINE BLUE AND KPVS UPON CONTACT WITH STANDARDIZED SOLUTIONS

| Specific Gravity of Standardized Solution | Ionic Strength (molar) | Observed Color |
| --- | --- | --- |
| 1.000 | 0 | red-violet |
| 1.005 | 0.125 | blue-purple |
| 1.015 | 0.5 | dull blue |
| 1.025 | 1 | sky blue |
| 1.040 | 1.5 | bright sky blue |

However, three clinical studies involving a total of about 200 urine samples showed that the correlation between a specific gravity assay performed instrumentally (the refractive index method) and a specific gravity assay performed by measuring urine ionic strength, as described above, is good in low to medium specific gravity ranges. The correlation however decreases in the high specific gravity range. Therefore, a reagent strip designed to measure only ionic strength would not provide an accurate high specific gravity assay. However, in accordance with the present invention, a reagent strip that is sensitive both to test sample ionic strength and buffer capacity was found to have better correlation to high specific gravity urines and thereby improve the accuracy of specific gravity assays.

Therefore, in accordance with the present invention, to perform a dry phase, test strip assay for specific gravity, the reagent composition first is produced. A reagent composition is produced by simply admixing composition ingredients to provide an aqueous, alcoholic, or hydroalcoholic solution including a sufficient amount of the acid form of a strong polyelectrolyte, like poly(styrenesulfonic acid), to provide a buffered pH of about 3 or less, and an indicator that responds to the metal cation concentration of the test sample and, for a test sample having a specific gravity of about 1.015 or greater, to pH changes attributed to test sample buffer capacity. Preferably, the solution is a hydroalcoholic solution, including at least about .50% by weight alcohol.

A reagent composition comprising a metachromatic dye that also is sensitive to pH changes, or a combination of a metachromatic dye and a pH indicator dye, and a strong polyelectrolyte, as described above, can be used in dry phase, test pad assays for ionic strength or specific gravity. A dry phase, test pad assay utilizing the reagent composition is performed in accordance with methods well known in the art. In general, the assay for ionic strength or specific gravity is performed by contacting the urine or other test sample with an analyte detection device that includes the reagent composition. The analyte detection device can be dipped into the test sample, or the test sample can be applied to the analyte detection device dropwise. The resulting change in color of the analyte detection device reveals the ionic strength, or specific gravity, of the test sample; and, if so designed, the resulting color transition can be compared to a standardized color chart to provide a measurement of the ionic strength or specific gravity of the urine or test sample.

Typically, the analyte detection device is a test strip impregnated with a reagent composition, designed either as a single pad test strip (to assay only for a single analyte) or as a multiple pad test strip (to assay for several analyses simultaneously). For either type of test strip, the test strip includes a support strip, or handle, normally constructed from a hydrophobic plastic, and a reagent test pad, comprising a bibulous or nonbibulous carrier matrix. In general, the carrier matrix is an absorbent material that allows the test ample to move, in response to capillary forces, through the matrix to contact the reagent composition and produce a detectable and measurable color transition.

The carrier matrix can be any substance capable of incorporating the chemical reagents required to perform the assay of interest, as long as the carrier matrix is substantially inert with respect to the chemical reagents and does not contaminate the urine or other test samples either by test sample extraction of components comprising the carrier matrix or by appreciably altering the urine or test sample in a way to make the subsequent assays inconclusive, inaccurate or doubtful. The carrier matrix also is porous or absorbent relative to the liquid test sample.

The expression "carrier matrix" refers either to bibulous or nonbibulous matrices that are insoluble in water and other physiological fluids and that maintain their structural integrity when exposed to water and other physiological fluids. Suitable bibulous matrices include filter paper, sponge materials, cellulose, wood, woven and nonwoven fabrics, and the like. Nonbibulous matrices include glass fiber, polymeric films, and microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulose beads, and especially fiber-containing papers such as filter paper or chromatographic paper; synthetic or modified naturally-occurring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. The carrier matrix can be of different chemical compositions or a mixture of chemical compositions. The matrix also can vary in regards to smoothness and roughness combined with hardness and softness. The handle usually is formed from hydrophobic materials such as cellulose acetate, polyethylene terephthalate, polycarbonate or polystyrene, and the carrier matrix is most advantageously constructed from filter paper or polymeric films.

To achieve the full advantage of the present invention, the reagent composition is incorporated into a suitable carrier matrix to provide a test pad, and the test pad is utilized in a dry phase test strip for the ionic strength or specific gravity assay of an aqueous test sample. The method of the present invention provides an economical, accurate and reliable assay of aqueous test samples that can be performed at home or in the laboratory. In addition, the method of the present invention allows the differentiation and measurement of test sample ionic strength or specific gravity, therefore making the specific gravity assay more useful clinically.

In accordance with the method of the present invention, to perform a dry phase, test strip assay for ionic strength or specific gravity, the aqueous, alcoholic, or hydroalcoholic reagent composition described above, including about 0.1 to about 0.7 mM of an indicator dye capable of exhibiting metachromasia and of responding to a pH change attributable to buffer capacity, such as thionin, quinoldine red, methylene blue, or astrazon orange; and 0.5% to about 4%, by weight, of a strong polyelectrolyte, in the acid form, like a poly(vinyl sulfonic acid), first is prepared. A bibulous matrix, such as filter paper, like WHATMAN CCP500 filter paper, available commercially from Whatman Ltd., Maidstone, Kent, U.K., then is saturated with the reagent composition including the indicator and the strong polyelectrolyte either by spreading, by immersing or by spraying the reagent composition onto precut strips of the filter paper. After removing the aqueous, alcoholic or hydroalcoholic carrier by oven drying in an air oven at about 50° C. for about 15 to 20 minutes, the filter paper incorporating the reagent composition is cut to an appropriate size, such as a pad having dimensions of about 0.25 cm by about 0.25 cm to about 1 cm by about 1 cm. The filter paper incorporating the reagent composition then is secured to an opaque or transparent hydrophobic plastic handle with double sided adhesive tape.

The resulting test strip then was dipped into a fresh, uncentrifuged urine sample for a sufficient time to saturate the test pad with the sample. After waiting a predetermined time, such as about thirty seconds to about two minutes, the test strip is examined, either visually or instrumentally, for a response. The degree and intensity of the color transition of the test pad reveal the ionic strength, or, if desired, the specific gravity, of the urine sample.

In accordance with another important feature of the present invention, it is well within the experimental techniques of those skilled in the art of preparing resin devices to determine the proper balance between size of test pad; the strength of reagent composition; the identity and amount of the indicator and the strong polyelectrolyte in the reagent composition; the amount of test sample; and the method of introducing the test sample to the test strip, such as by pipetting rather than dipping, to provide detectable and differentiable color transitions, such that a comparison, either visually or instrumentally, to color standards derived from solutions of known ionic strength or specific gravity is possible.

In many cases simple visual observation of the test strip provides the desired information. If more accurate information is required, a color chart bearing color spots corresponding to various standard ionic strengths or specific gravities can be prepared for the particular reagent composition used in the test strip. The resulting color of the test strip after contact with the urine sample then can be compared with the color spots on the chart to determine the ionic strength or specific gravity of the test sample.

If a still more accurate determination is required, a spectrophotometer or colorimeter can be used to more precisely determine the degree and intensity of the color transition. In addition, the dry phase, reagent strip assay can be made quantitative by employing spectrophotometric or colorimetric techniques, as opposed to visual techniques, in order to more reliably and more accurately measure the degree and intensity of the color transition, and therefore more accurately measure the ionic strength or specific gravity of the test sample.

To show the new and unexpected results achieved by using a reagent composition of the present invention in a method of determining the ionic strength or specific gravity of a test sample, color space plots were prepared from assays using dry phase test strips comprising a test pad incorporating a reagent composition including either a single metachromatic dye or a combination of metachromatic dyes, and a polyelectrolyte, into a filter paper matrix. The color space plots were obtained by contacting solutions of known ionic strength or specific gravity with the dry phase test strips including the present reagent composition incorporated into a filter paper carrier matrix.

In general, a color space plot includes three axes, the $L^*$, $A^*$ and $B^*$ axes. The values of $L^*$, plotted on the vertical axis are a measure of the intensity of color, whereby a large $L^*$ value denotes a light color and $L^*=0$ denotes a completely black color. The horizontal $A^*$ axis is a measure of the color transition from green to red, whereby the more positive the $A^*$ value, the more red the color, and analogously, the more negative the $A^*$ value, the more green the color. Similarly, the third axis, $B^*$, is a measure of the color transition from blue to yellow, whereby the greater the value of $B^*$, the more yellow the color, and analogously the smaller the value of $B^*$, the more blue the color.

The color space difference ($\Delta E$) is calculated from the following equation (Eq. 2):

$$\Delta E = \sqrt{(L_1^* - L_2^*)^2 + (A_1^* - A_2^*)^2 + (B_1^* - B_2^*)^2} \quad \text{Eq. 2}$$

wherein:

$L_1^*$, $A_1^*$, and $B_1^*$ are the color space values determined for a first standardized solution of known specific gravity or ionic strength;

$L_2^*$, $A_2^*$ and $B_2^*$, are the color space values determined for a second standardized solution of known specific gravity or ionic strength having a different specific gravity or ionic strength from the first standardized solution; and $\Delta E$ is the color space difference between the color space plots of the first and second standardized solutions.

The color space difference ($\Delta E$) is the straight line distance between two points in a three-dimensional color space plot. Theoretically, a color space difference of one (1) unit is the smallest color space difference the human eye can distinguish. However, because of the inherent differences between the visual capabilities of individuals, a color space difference ($\Delta E$) of about 3 units is required in order to practically and confidently distinguish between colors.

The $L^*$, $A^*$ and $B^*$ values plotted on the color space plots are calculated from the different reflectance measurements taken at sixteen different wavelengths evenly spaced between 400 and 700 nm (nanometers) using standard equations well-known in the art. In general, the percent reflectance at each of the sixteen different wavelengths is multiplied by the intensity of the light at that wavelength. These values then are multiplied by standard weighing functions for the colors red, green and blue, and finally added together. These calculations yield three tristimulus values, X, Y and Z. $L^*$, $A^*$ and $B^*$ are calculated from the X, Y and Z tristimulus values using the following equations:

$$L^* = 116 \times [(Y/Y_o)^{\frac{1}{3}} - 16)] \quad \text{(Eq. 3)}$$

$$A^* = 500 \times [(X/X_o)^{\frac{1}{3}} - (Y/Y_o)^{\frac{1}{3}}] \quad \text{(Eq. 4)}$$

$$B^* = 200 \times [(Y/Y_o)^{\frac{1}{3}} - (Z/Z_o)^{\frac{1}{3}}] \quad \text{(Eq. 5)}$$

wherein:

$X_o$, $Y_o$ and $Z_o$ are the tristimulus values for perfect white (i.e., reflectance $=100\%$ at all wavelengths), and X, Y and Z are the tristimulus values calculated as described above from the sixteen wavelengths between 400 and 700 nm.

From the color space plots, the color space differences ($\Delta E$) were calculated, and are summarized and discussed in more detail hereinafter. In interpreting the data to be presented, a term such as $\Delta E$ (1.007–1.022) is the color space difference between specific gravity assays for standardized urine solutions having a specific gravity of 1.007 and 1.022. Similarly, the term $\Delta E$ (0–0.12) is the color space difference between assays of standardized solutions having a sodium chloride concentration of 0M and 0.12M respectively. The terms $\Delta E$ (0.12–0.5) and $\Delta E$ (0.5–3) are analogously defined.

To demonstrate the unexpected results provided by a reagent composition of the present invention, the following compositions of Examples 1 and 2 first were prepared. Then two sets of test strips were prepared, and used to assay for specific gravity and ionic strength of a test sample. Both sets of test strips utilized filter paper (WHATMAN CCP500) as the carrier matrix of the test pad.

EXAMPLE 1

One-half milliliter of a 1.5% by weight aqueous solution of potassium poly(vinyl sulfate) (KPVS) was admixed with 2 milliliters (ml) of distilled water. The resulting aqueous solution of KPVS then was admixed with 15 ml of methanol. Aqueous solutions of the metachromatic dyes thionin and astrazon orange were added, individually, to the methanol-water solution of KPVS to provide a reagent composition having a concentration of 2.5 mM KPVS (as negatively-charged monomeric subunits), 0.6 mM thionin and 0.13 mM astrazon orange. The carrier of the reagent composition was 92% by weight methanol. The presence of a high percentage of methanol and the order of addition of the ingredients help prevent the precipitation of thionin by the KPVS.

EXAMPLE 2

The procedure utilized in Example 1 was repeated to provide a reagent composition having a concentration of 5 mM KPVS (as negatively-charged monomeric subunits) and 0.075 mM toluidine blue.

The compositions of Examples 1 and 2 each were incorporated into filter paper (WHATMAN CCP500), and the filter paper including either the composition of Example 1 or the composition of Example 2 was dried by standard procedures. The composition of Example 1 includes two metachromatic dyes and demonstrated an excellent sensitivity to test samples having a wide range of ionic strengths and specific gravities. However, the correlation between ionic strength and specific gravity decreased as the specific gravity of the test samples increased. The composition of Example 2, including one metachromatic dye, demonstrated an excellent sensitivity to test samples having a relatively low ionic strength or specific gravity.

Individual test strips incorporating either a composition of Example 1 or a composition of Example 2 were dipped into standardized sodium chloride solutions having a concentration of 0, 0.125, 0.5 or 3M sodium chloride and into standardized urine solutions having a specific gravity of 1.007 or 1.002. The resulting color transition of each test strip was determined and converted into $\Delta E$ units by standard procedures known in the art. The $\Delta E$ units for these experiments are summarized in TABLE II.

TABLE II $\Delta E$ DIFFERENCES FOR ASSAYS UTILIZING A COMPOSITION OF EXAMPLES 1 AND 2

| Example | NaCl Concentration (M) | | | Urine Specific Gravity $\Delta E$ (1.007–1.022) |
|---|---|---|---|---|
| | $\Delta E$ (0–0.125) | $\Delta E$ (0.125–0.5) | $\Delta E$ (0.5–3) | |
| 1 | 7 | 13 | 25 | 5 |
| 2 | 12 | 12 | 3 | 10 |

In accordance with the method and composition of the present invention, from TABLE II, by including a metachromatic dye and a polyelectrolyte in a reagent composition to assay for ionic strength or specific gravity, the color space differences are at or above the minimum human detectable limit of approximately three $\Delta E$ units, thereby providing an ionic strength assay or specific gravity assay of the test sample. Generally, the color space difference values are at or above 3, therefore a color change is discernible by the human eye, and the assayer easily can differentiate between urine samples having different ionic strengths or specific gravities.

Specifically, a test strip including the composition of Example 1, incorporating a reagent composition including a combination of metachromatic dyes, showed an excellent sensitivity to sodium ions in the range of 0 to 0.125M that is perceptible to the human eye ($\Delta E=7$). The test strips also showed a sensitivity to sodium ions in the range of 0.125 to 0.5 M ($\Delta E=13$) and in the range of 0.5 to 3M ($\Delta E=25$) that is readily perceptible to the human eye, thereby allowing an assayer to distinguish between test samples including 0.125M, 0.5M or 3M sodium ions. Similarly, an assayer can easily distinguish between a urine sample having a specific gravity of 1.007 and a sample having a specific gravity of 1.002 because the color space difference ($\Delta E$) is a readily perceptible 5 units.

Test strips incorporating the composition of Example 2, including a single metachromatic dye, demonstrated an increased sensitivity to sodium ions present in a concentration of about 0.125M or less ($\Delta E=12$). However, sensitivity to sodium ion concentrations above about 0.5M is minimal, as demonstrated by the $\Delta E$ (0.5–3) value for sodium ion of 3. Because the $\Delta E$ values are small, an assayer would have difficulty distinguishing between a test sample that is 0.5M in sodium ion and 3M in sodium ion. However, an assayer could detect and measure a sodium ion concentration below 0.125M because the color space difference exhibited is well above the minimum detectable level of 3 color space units.

It also should be noted that the $\Delta E$ (1.007–1.002) value of 10 in the specific gravity assay using a test strip incorporating the composition of Example 2 was greater than the $\Delta E$ (1.007–1.002) value (i.e., 5) using a test strip incorporating a composition of Example 1. This greater $\Delta E$ value translates into a more easily differentiable color transition and therefore a more sensitive specific gravity assay. The more differentiable color transition is attributed to weaker dye binding to the polyelectrolyte.

The results tabulated in TABLE II are illustrated in FIG. 1. FIG. 1 shows that the color transition for the reagent composition of Example 1 ranges from the red-yellow quadrant into the green-blue quadrant over the concentration range of 0 to 3M sodium chloride. The reagent composition of Example 2 undergoes a color transition from the blue-red quadrant into the blue-green quadrant over the concentration range of 0 to 3M sodium chloride. The color transitions for the reagent compositions of Examples 1 and 2 therefore are readily detectable, and differentiable, either visually or instrumentally.

The above-described assays for specific gravity using a composition of Example 1 or 2 provided accurate results for low to medium specific gravity test samples. However, because the assay directly measured ionic strength, and only indirectly measured specific gravity, and because the correlation of ionic strength to specific gravity decreases with increasing specific gravity, the accuracy of the specific gravity assays of test samples having a specific gravity of about 1.015 or greater decreased. The decrease in assay accuracy for high specific gravity test samples has been attributed to test sample buffer capacity, and accordingly, the above-described ionic strength assay for specific gravity has been modified and improved to include the effects of test sample buffer capacity on high specific gravity test samples.

Therefore, the present invention combines the primary color transition resulting from the pH-independent release of a metachromatic dye from a polyelectrolyte caused by metal cations present in the test sample, with a secondary color transition attributable to the buffer capacity of the test sample causing a pH change. The primary pH-independent color transition attributable to the polyelectrolyte-metachromatic dye interactions in response to test sample ionic strength, is combined with a secondary color transition of the indicator attributable to test sample buffer capacity in response to a change in pH. To achieve this result, the operating pH range of the reagent composition is at a pH of about 3 or less, which is achieved, at least in part, by including a sufficient amount of the acid form of a strong polyelectrolyte in the reagent composition.

Accordingly, the following compositions of Examples 3 through 13 were prepared. The compositions of Examples 3 through 13 include sufficient amounts of the acid form of a strong polyelectrolyte to provide a buffered pH of about 1.5 to about 2. The compositions of Examples 3 through 13 exhibit only a pH-independent metachromatic color transition for test samples having a low to medium specific gravity of less than about 1.015. For low to medium specific gravity test samples, the buffer capacity has a negligible effect on the color transition of reagent composition or on the correlation of ionic strength to specific gravity.

However, the compositions of Examples 3 through 13 exhibit both a primary metachromatic color transition and a secondary pH change-induced color transition which is attributed to test sample buffer capacity and which supplements the primary metachromatic color transition for high specific gravity test samples. The color transition induced by a pH change thereby improves the correlation of ionic strength to specific gravity, and provides a more accurate assay of high specific gravity test samples.

From Examples 3-13 it is noted that considerably larger $\Delta E$ values are exhibited in the specific gravity range of 1.005 to 1.024 than in Examples 2 and 3. A specific gravity of 1.005 to 1.024 is the common range for urine. The larger $\Delta E$ values demonstrate that distinguishing between different specific gravities is easier and more accurate when the indicator comprises a combination of both a metachromatic and pH indicator dye.

Therefore, the compositions of Examples 3 through 13 inhibit pH changes induced by low to medium specific gravity urines and only are affected by pH changes attributable to the buffer capacity of high specific gravity urines. Furthermore, in various compositions of Examples 3 through 13, the color transition for high specific gravity urine samples was optimized by incorporating a second pH indicator dye having a $pK_a$ about 1 unit greater than the $pK_a$ of a first pH indicator dye.

The compositions of Examples 3 through 13 were prepared in an identical manner to the compositions of Examples 1 and 2, and then were incorporated into a filter paper carrier matrix (WHATMAN CCP500) in the manner described above. The compositional makeup of the compositions of Examples 3-13 are summarized in Table III, which also includes the results of specific gravity assays using test strips incorporating the compositions of Examples 3-13. The test samples were laboratory-prepared solutions that essentially duplicate the ionic strength and buffer capacity of a clinical urine sample having a particular specific gravity.

TABLE III

| Example | Polyelectrolyte[1] Type | % (by weight) | Primary Dye Type | [mM][4] | Secondary Dye Type | (0.2 mM) | Buffer [M][4] |
|---|---|---|---|---|---|---|---|
| 3 | PSS[2] | 2 | Crystal Violet | 0.25 | | | 0.1 Phosphate |
| 4 | PSS | 1.5 | STAINS-ALL | 0.75 | Yellow #5 | | 0.1 Phosphate |
| 5 | PSS | 2 | New Fuschin | 0.50 | | | |
| 6 | PSS | 1.5 | STAINS-ALL | 0.75 | | | 0.1 Phosphate |
| 7 | PSS | 2.5 | STAINS-ALL | 0.63 | New Fuschin | | |
| 8 | PSS | 2 | New Fuschin | 0.25 | DMASP[5] | | 0.1 Sarcosine |
| 9 | PSS | 1.5 | STAINS-ALL | 0.75 | | | 0.2 Phosphate |
| 10 | PSS | 2 | New Fuschin | 0.50 | Quinaldine Red | | 0.2 Citraconic |
| 11 | PAMPSA[3] | 2 | Pinacyanol Bromide | 0.50 | | | 0.15 Phosphate |
| 12 | PAMPSA | 2 | Quinaldine Red | 0.75 | | | |
| 13 | PSS | 1.5 | New Fuschin | 0.25 | | | 0.1 Phosphate |

| Example | L*a*b* Correlation[6] | $\Delta E$ (1.000–1.005) | $\Delta E$ (1.005–1.015) | $\Delta E$ (1.015–1.024) | $\Delta E$ (1.024–1.030) | Sum of $\Delta E$ (low to high) | OBSERVED COLOR CHANGE BETWEEN LOW & HIGH SPECIFIC GRAVITY |
|---|---|---|---|---|---|---|---|
| 3 | 0.93 | 12.4 | 22.1 | 19.8 | 15.5 | 70 | green to blue |
| 4 | 0.89 | 12.4 | 23.5 | 21.6 | 4.9 | 62 | yellow to dark red |
| 5 | 0.92 | 15.4 | 18.2 | 20 | 11.3 | 65 | blue-grey to magenta |
| 6 | 0.94 | 13.3 | 26.2 | 20.6 | 5.8 | 66 | white to red |
| 7 | 0.93 | 8 | 18.4 | 23.2 | 13.9 | 64 | blue-gray to dark red |
| 8 | 0.91 | 11.7 | 11.6 | 13.2 | 10.7 | 47 | violet to bright pink |
| 9 | 0.89 | 8.5 | 22.2 | 21 | 5 | 57 | white to red |
| 10 | 0.95 | 14 | 17.5 | 12 | 9.8 | 53 | blue-gray to red |
| 11 | 0.90 | 11.8 | 18.8 | 19.8 | 6.2 | 57 | white to purple |
| 12 | 0.90 | 13.6 | 14.9 | 15.4 | 6 | 50 | white to red |
| 13 | 0.96 | 10.3 | 13.2 | 11.3 | 6.1 | 41 | blue-grey to |

TABLE III-continued magenta

[1] as the acid-form;
[2] PSS-polystryenesulfonic acid;
[3] PAMPSA-poly(2-acrylamido-2-methyl-propanesulfonic acid);
[4] mM-millimolar, M-molar;
[5] DMASP-2-[4-dimethylaminostyrl]-1-methylpyridinium iodide;
[6] L*a*b* correlation is the R (correlation coefficient) value obtained by a multiple linear regression of L*,a*,b* versus measured specific gravity measured instrumentally by refractive index, this result gives a measure of the observed color to urine specific gravity correlation.

Table III illustrates that the ΔE values are sufficiently great to produce a detectable and differentiable color transition, and that the color transition correlates well to urine specific gravity. In another test, a group of 25 selected clinical urine samples having a specific gravity between 1.002 and 1.030 also were tested with each of the compositions of Examples 3-13. A multiple linear regression of L*a*b* versus urine specific gravity determined instrumentally by refractive index was calculated. Each composition of Examples 3 through 13 gave a high correlation coefficient (R-value), thereby indicating an accurate specific gravity assay. Unexpectedly, even high specific gravity urines were assayed accurately because the combination of strong polyelectrolyte and indicator, buffered at pH of about 3 or below, included both ionic strength and buffer capacity in the assay. Accordingly, the present invention overcomes a serious problem encountered in prior specific gravity assays based on polyelectrolytes and indicator dyes that measured only the ionic strength of the test sample and then correlated ionic strength to specific gravity.

Correlation coefficients of the composition of Example 2 with specific gravity was found to be 0.83, with a much smaller overall ΔE range of 30. This correlation is lower than any of the correlation coefficients found in the compositions of Examples 3-13, and again demonstrates the advantages of using an indicator the measures ionic strength (i.e., a metachromatic color transition) and buffer capacity (a pH indicator color transition).

The compositions of Examples 14 and 15 also were prepared and incorporated into a filter paper carrier matrix as described above. The compositions of Examples 14 and 15 include poly(2-acrylamido-2-methyl-propanesulfonic acid) (PAMPSA), in the acid form, as the polyelectrolyte. The compositions also include methylene blue as the primary metachromatic dye to optimize the color transition of the reagent composition, and further include 2-[4-dimethylamino)styrl]-1-methylpyridinium iodide (DMASP), a yellow pH sensitive metachromatic dye for high specific gravity sensitivity, and quinaldine red, an ion sensitive dye for low specific gravity sensitivity. The response of test strips incorporating the compositions of Examples 14 and 15 to urine pools is summarized in Table IV.

TABLE IV

| Example | ΔE (1.005 to 1.015) | ΔE (1.015 to 1.025) | Ingredients |
|---|---|---|---|
| 14 | 14 | 10 | 1.5% PAMPSA, 2 mM DMASP, 0.025 mM Quinaldine Red, .05 mM Methylene Blue |
| 15 | 23 | 33 | 1.5% PAMPSA, 2 mM DMASP, 0.025 mM Quinaldine Red, .25 mM Methylene Blue |

The ΔE values summarized in Table IV are far above the minimal detectable limit, and provide a detectable and differentiable color transition. The presence of three indicator dyes enhanced the sensitivity of the assay and provided more accurate high specific gravity assays.

Figure 2:
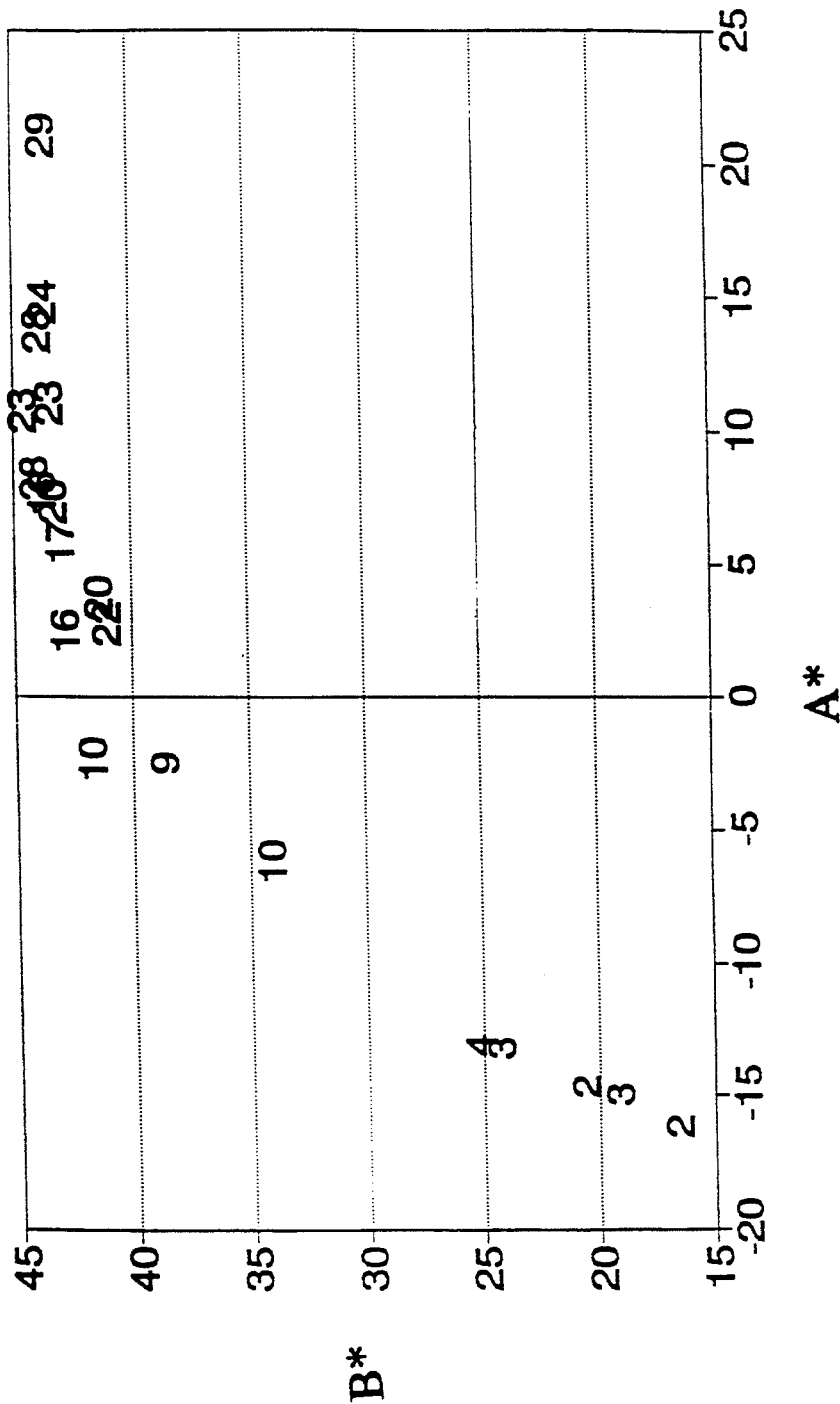
FIG. 2 is a two dimensional color space plot of A* vs. B* illustrating the color transition of a reagent composition comprising polystyrenesulfonic acid and new fuchsin in response to test samples of different specific gravity.

Another experiment is illustrated in FIG. 2. FIG. 2 is a plot of A* vs. B* for a reagent composition including 2% by weight polystyrenesulfonic acid as the polyelectrolyte, and 0.5 mM of new fuchsin as the indicator dye. The reagent composition was used to assay various urine samples having different specific gravities. The numerals plotted in FIG. 2 represent the urine specific gravity of the test sample. The urine specific gravity was measured instrumentally and, for ease and clarity, plotted as (1-SG)(1000), wherein SG is specific gravity. Accordingly, a urine specific gravity of 1.010 is plotted in FIG. 2 as 10, and a urine specific gravity of 1.020 is plotted as 20.

The plot in FIG. 2 illustrates that with increasing specific gravity the color transition changes from the green-blue quadrant through the green-yellow quadrant to the red-yellow quadrant. Accordingly, the reagent composition can accurately assay urine samples for specific gravity at least over the range of about 1.000 to about 1.040.

As a result, using a suitable indicator and sufficient amount of a strong polyelectrolyte in a reagent composition buffered at a pH of about 3 or less, allows the fast and reliable differentiation and measurement of the ionic strength or specific gravity of test samples. The present reagent compositions provide an important and useful benefit of providing a sensitive and accurate ionic strength assay and a quantitative specific gravity assay. As illustrated above, the indicator included in the reagent composition responds directly to the metal cation concentration of the test sample (which is essentially independent of pH) and to a pH change induced by the buffer capacity of high specific gravity test samples, and thereby provides a quantitative specific gravity or ionic strength assay.

It should be understood that those skilled in the art of designing test kits are able to design an optimal test strip incorporating a sufficient amount of a particularly effective reagent composition to permit the differentiation and measurement of test sample ionic strengths and specific gravities. An assay utilizing the method and composition of the present invention exhibits a color space difference of at least 3 units. This ΔE value is sufficient for detection by the human eye, and is easily detected by present day colorimeters or spectrophotometers. Similarly, the method and composition of the present invention provide an accurate ionic strength or specific gravity assay regardless of varying amounts of nonionic components, such as glucose or albumin, found in the test sample, as long as a sufficient number of metal cations are present in the test sample.

In accordance with another important feature of the present invention, full color development of a test strip including a present reagent composition occurs within about one-half minute to about two minutes after contacting the test strip with the test sample. Maximum color development occurs after about two minutes of contact. However, acceptable and trustworthy assay results are achieved when the test strip is examined for a color change about one-half minute after contact with the test sample. Such a short time for full color development of the test strip is an additional advantage of the reagent composition of the present invention. In addition, the color transition is sufficiently stable such that an accurate assay results from examining the test strip up to ten minutes after contacting the test sample. Therefore, test strips incorporating the reagent composition of the present invention can be used to obtain fast and more accurate ionic strength assays and semiquantitative specific gravity assays.

Overall, using a combination of a metachromatic and a pH indicator dye, or using a metachromatic dye that also can act as a pH indicator dye, and the acid form of a strong polyelectrolyte in a reagent composition incorporated into a suitable carrier matrix, such as filter paper, provides excellent sensitivity to the ionic strength and specific gravity of aqueous test samples. In addition to excellent sensitivity, the method and composition of the present invention provide full color development and accurate assay results in a relatively short time.

Therefore, in accordance with an important feature of the present invention, more accurate and reliable assays for ionic strength and specific gravity of urine and other liquid test samples can be performed by utilizing a suitable indicator and a strong polyelectrolyte in a reagent composition buffered to a pH of about 3 or less. The indicator dye and polyelectrolyte improve the color differentiation between test samples having different ionic strengths and specific gravities, and are essentially independent of test sample pH, thereby improving assay sensitivity.

Obviously, many modifications and variations of the invention as hereinbefore set forth can be made without departing from the spirit and scope thereof and therefore only such limitations should be imposed as are indicated by the appended claims.

What is claimed is:

1. A composition capable of exhibiting a detectable and measurable, pH-independent color transition in response to a metal cation concentration and a buffer capacity of an aqueous test sample, said composition comprising:
   (a) about 5 to about 100 millimoles per liter of an indicator selected from the group consisting of:
      (i) a metachromatic dye that is responsive to a change in pH,
      (ii) a combination of a metachromatic dye and a pH indicator dye, and
      (iii) mixtures thereof;
   (b) a sufficient amount of a polyelectrolyte having negatively-charged sites to which the metachromatic dye binds; and
   (c) a carrier comprising water, a water miscible alcohol or a mixture thereof,
   wherein the composition is buffered at a pH of about 3 or less by a buffer including a sufficient amount of an acid form of the polyelectrolyte to achieve said pH range, and
   wherein the composition undergoes a primary pH-independent color transition in response to the metal cation concentration of the test sample and a secondary color transition in response to the buffer capacity of the test sample.

2. The composition of claim 1 further comprising:
   (d) 0 to about 600 millimoles per liter of a buffer having a $pK_a$ of about 5 or less.

3. The composition of claim 1 wherein the metachromatic dye is a cationic metachromatic dye.

4. The composition of claim 1 wherein the metachromatic dye is selected from the group consisting of thionin, astrazon orange, astrazon blue, toluidine blue, methylene blue, acridine orange, pyronine-G, proflavine, azure A, phloxine B, cresyl violet, safranine O, neutral red, thioflavin T, fast red AL, methylene green, rhodamine B, rhodamine 6G, azure B, indoine blue, brilliant cresyl blue, 4',6-diamidino-2-phenylindole dihydrochloride hydrate, acridine yellow, acriflavine, pyronin-Y, pyronin-B, meldola's blue, nile blue, nile red, new methylene blue, methyl violet, a triphenylmethane dye, methyl green, crystal violet, victoria blue, brilliant green, basic fuchsin, new fuchsin, ethyl violet, malachite green oxalate, quinaldine red, pinacryptol yellow, pinacyanol bromide, pinacyanol chloride, 2-[4-(dimethylamino)styrl]-1-methylquinolium iodide, 2-[4-(dimethylamino)styrl]-1-methylpyridinium iodide, stains-all, benzopurpurin, methyl green, and mixtures thereof.

5. The composition of claim 1 wherein the pH-responsive metachromatic dye undergoes a color transition in response to a pH change at a pH of about or less.

6. The composition of claim 1 wherein the pH-responsive metachromatic dye is selected from the group consisting of neutral red, basic fuchsin, new fuschin, benzopurpurin, quinaldine red, pinacyanol bromide, pinacyanol chloride, 2-[4-(dimethylamino)styrl]-1-methylquinolium iodide, 2-[4-(dimethylamino)styrl]-1-methypyridinium iodide, stains-all, crystal violet, and mixtures thereof.

7. The composition of claim 1 wherein the pH-indicator dye responds to a pH change at a pH of about 4 or less.

8. The composition of claim 1 wherein the pH-indicator dye is selected from the group consisting of methyl green, victoria blue, brilliant green, ethyl violet, malachite green oxalate, metanil yellow, xylenol blue, methyl violet 2B, benzyl orange, bromphenol red, bromocresol green, thymol blue, and m-cresolsulfonephthalein, and mixtures thereof.

9. The composition of claim 1 wherein the indicator comprises a first and a second dye, wherein each dye is responsive to a change in pH and the second dye has a $pK_a$ about one to about two units greater than the first dye, and wherein at least one of the first and the second dye is a metachromatic dye.

10. The composition of claim 7 wherein the first dye and the second dye are selected from the group consisting of neutral red, basic fuchsin, new fuschin, benzopurpurin, quinaldine red, pinacyanol bromide, pinacyanol chloride, 2-[4-(dimethylamino)styrl]-1-methylquinolium iodide, 2-[4-(dimethylamino)styrl]-1-methypyridinium iodide, stains-all, crystal violet methyl green, victoria blue, brilliant green, ethyl violet, malachite green oxalate, metanil yellow, xylenol blue, methyl violet 2B, benzyl orange, bromphenol red, bromocresol green, thymol blue, m-cresolsulfonephthalein, and mixtures thereof.

11. The composition of claim 1 wherein the polyelectrolyte is in the acid form.

12. The composition of claim 1 wherein the polyelectrolyte is present in a concentration of about 0.5% to about 4%, by weight of the composition.

13. The composition of claim 1 wherein the polyelectrolyte is present in a concentration of about 1% to about 3%, by weight of the composition.

14. The composition of claim 1 wherein the polyelectrolyte is selected from the group consisting of a poly(vinyl sulfate), a poly(vinyl sulfonate), a poly(styrenesulfonate), a poly(2-acrylamido-2-methyl-1-propanesulfonic acid), and mixtures thereof.

15. The composition of claim 14 wherein the electrolyte is in the acid form.

16. The composition of claim 2 wherein the buffer has a $pK_a$ with in about two units of the $pK_a$ of the electrolyte and is selected from the group consisting of glycine, lysine, citraconic acid, sarcosine, phosphonic acid, an amino acid buffer, trichloracetate, sulfosalicylate, phosphate, tartarate, citrate, succinate, maleic acid, 2,2-bis(hydroxymethyl)-2,2',2''-nitrilotriethanol, 3,3-dimethylglutaric acid, and mixtures thereof.

17. The composition of claim 1 wherein the carrier further comprises 0% to about 50% by weight of the carrier of an organic solvent.

18. The composition of claim 1 buffered at a pH of about 2 or less.

19. A method of determining the specific gravity of an aqueous test sample by measuring an ionic strength and a buffer capacity of the test sample, said method comprising:
  (a) contacting an aqueous test sample, wherein the aqueous test sample has a specific gravity of about 1.000 to about 1.040, with a reagent composition, said composition comprising:
    (i) about 5 to about 100 millimoles per liter of an indicator selected from the group consisting of:
      (A) a metachromatic dye that is responsive to a change in pH,
      (B) a combination of a metachromatic dye and a pH indicator dye, and
      (C) mixtures thereof;
    (ii) a sufficient amount of polyelectrolyte having negatively-charged sites to which the metachromatic dye binds; and
    (iii) a carrier comprising water, a water miscible alcohol or a mixture thereof,
  wherein the composition is buffered at a pH of about 3 or less by a buffer including a sufficient amount of an acid form of the polyelectrolyte to achieve said pH range, and wherein a composition undergoes a primary pH-independent color transition in response to a metal cation concentration of the test sample and a secondary color transition in response to the buffer capacity of the test sample; and
  (b) correlating the specific gravity of the aqueous test sample to the intensity and degree of the primary and secondary color transition of the reagent composition.

20. The method of claim 19 wherein the reagent composition further comprises:
  (iv) 0 to about 600 millimoles per liter of a buffer having a $pK_a$ of about 5 or less.

21. The method of claim 19 wherein the aqueous test sample is a biological fluid.

22. The method of claim 21 wherein the biological fluid is selected from the group consisting of urine, blood plasma, blood serum, and perspiration.

23. The method of claim 19 wherein the indicator comprises a cationic metachromatic dye that is responsive to a pH change at a pH of about 4 or less.

24. The method of claim 19 wherein the polyelectrolyte is present in a concentration of about 0.5% to about 4%, by weight of the composition.

25. The method of claim 19 wherein the intensity and degree of the primary and secondary color transition are determined visually or instrumentally.

26. A method of quantitatively determining the specific gravity of an aqueous metal cation-containing sample by measuring a metal cation content and a buffer capacity of the sample, comprising:
  (a) contacting an aqueous sample, wherein the aqueous test sample has a specific gravity of about 1.000 to about 1.040, with an analyte detection device comprising a test pad having incorporated therein:
    (i) about 5 to about 100 millimoles per liter of an indicator selected from the group consisting of:
      (A) a metachromatic dye that is responsive to a change in pH,
      (B) a combination of a metachromatic dye and a pH indicator dye, and
      (C) mixtures thereof;
    (ii) a sufficient amount of polyelectrolyte having negatively-charged sites to which the metachromatic dye binds; and
    (iii) a carrier comprising water, a water miscible alcohol or a mixture thereof,
  wherein the composition is buffered at a pH of about 3 or less by a buffer including a sufficient amount of an acid form of the polyelectrolyte to achieve said pH range, and wherein the composition undergoes a primary pH-independent color transition in response to the metal cation concentration of the test sample and a secondary color transition in response to the buffer capacity of the test sample;
  (b) examining the analyte detection device for a total color transition in response to the metal cation content and the buffer capacity of the aqueous sample; and
  (c) correlating the total color transition to the specific gravity of the aqueous sample.

27. The method of claim 26 wherein the reagent composition further comprises:
  (iv) 0 to about 600 millimoles per liter of a buffer having a $pK_a$ of about 5 or less.

28. The method of claim 26 wherein the aqueous sample has a specific gravity of about 1.015 to about 1.040.

29. An analyte detection device to determine the specific gravity of an aqueous test sample, wherein the aqueous test sample has a specific gravity of about 1.000 to about 1.040, by measuring a metal cation concentration and a buffer capacity of the test sample, comprising:
  a support strip;
  a test pad; and
  a reagent composition incorporated into the test pad, said reagent composition comprising:
    (a) about 5 to about 100 millimoles per liter of an indicator selected from the group consisting of
      (i) a metachromatic dye that is responsive to a change in pH,
      (ii) a combination of a metachromatic dye and a pH indicator dye, and
      (iii) mixtures thereof;

(b) a sufficient amount of a polyelectrolyte having negatively-charged sites to which the metachromatic dye binds; and (c) a carrier comprising water, a water miscible alcohol or a mixture thereof, wherein the composition is buffered at a pH of about 3 or less by a buffer including a sufficient amount of an acid form of the polyelectrolyte to achieve said pH range, and wherein the composition undergoes a primary pH-independent color transition in response to the metal cation concentration of the test sample and a secondary color transition in response to the buffer capacity of the test sample.

30. The analyte detection device of claim 29 wherein the reagent composition further comprises:

(d) 0 to about 600 millimoles per liter of a buffer having a $pK_a$ of about 5 or less.

* * * * *

UNITED STATES PATENT AND TRADEMARK OFFICE
CERTIFICATE OF CORRECTION

PATENT NO. : 5,403,744
DATED : April 4, 1995
INVENTOR(S) : Chris T. Zimmerle

It is certified that error appears in the above-identified patent and that said Letters Patent is hereby corrected as shown below:

Claim 5, line 2, after "about" insert -- 4 --.

Signed and Sealed this

Third Day of October, 1995

Attest:

BRUCE LEHMAN

Attesting Officer   Commissioner of Patents and Trademarks